United States Patent [19]

Sytkowski et al.

[11] Patent Number: 6,153,407
[45] Date of Patent: *Nov. 28, 2000

[54] ERYTHROPOIETIN DNA HAVING MODIFIED 5' AND 3' SEQUENCES AND ITS USE TO PREPARE EPO THERAPEUTICS

[75] Inventors: Arthur J. Sytkowski, Arlington, Mass.; Jennifer Grodberg, Redwood City, Calif.

[73] Assignee: Beth Israel Deaconess Medical Center, Boston, Mass.

[*] Notice: This patent is subject to a terminal disclaimer.

[21] Appl. No.: 09/017,631

[22] Filed: Feb. 3, 1998

Related U.S. Application Data

[60] Continuation-in-part of application No. 08/808,881, Feb. 28, 1997, which is a division of application No. 08/383,743, Feb. 2, 1995, Pat. No. 5,614,184, which is a continuation-in-part of application No. 08/113,080, Aug. 26, 1993, abandoned, which is a continuation-in-part of application No. 07/920,810, Jul. 28, 1992, abandoned.

[51] Int. Cl.$^7$ ............................ C12N 15/16; C12N 15/67; A61K 38/18

[52] U.S. Cl. .................. 435/69.4; 536/23.51; 536/24.1; 530/350; 530/395; 514/2; 424/85.1

[58] Field of Search .............................. 536/23.51, 24.1; 530/351, 395; 514/2; 424/85.1; 435/67.4

[56] References Cited

U.S. PATENT DOCUMENTS

| | | |
|---|---|---|
| 4,677,195 | 6/1987 | Hewick et al. . |
| 4,703,008 | 10/1987 | Lin . |
| 4,732,889 | 3/1988 | Cynshi et al. . |
| 4,745,099 | 5/1988 | Akamatsu et al. . |
| 4,835,260 | 5/1989 | Shoemaker . |
| 4,954,437 | 9/1990 | Beck et al. . |
| 5,614,184 | 3/1997 | Sytkowski et al. ............... 424/85.1 |
| 5,688,679 | 11/1997 | Powell . |

FOREIGN PATENT DOCUMENTS

| | | |
|---|---|---|
| 2021528 | 7/1990 | Canada . |
| 0255231B1 | 2/1988 | European Pat. Off. . |
| 0267678A1 | 5/1988 | European Pat. Off. . |
| 0306943A3 | 9/1988 | European Pat. Off. . |
| 0409113 | 1/1991 | European Pat. Off. . |
| WO 91/05867 | 5/1991 | WIPO . |
| WO 92/21029 | 11/1992 | WIPO . |
| 94/02611 | 2/1994 | WIPO . |
| WO 94/24160 | 10/1994 | WIPO . |
| WO 94/25055 | 11/1994 | WIPO . |
| WO 95/25746 | 9/1995 | WIPO . |
| WO 95/33057 | 12/1995 | WIPO . |
| WO 99/02710 | 1/1999 | WIPO . |

OTHER PUBLICATIONS

Krystal, G., "A Simple Microassay for Erythropoietin Based on $^3$H–Thymidine Incorporation into Spleen Cells from Phenylhydrazine Treated Mice," *Exp. Hematol.*, 11(7): 649–660 (1983).

Jacobs, K., et al., "Isolation and Characterization of Genomic and cDNA clones of Human Erythropoietin," *Nature*, 313: 806–810 (1985).

Sytkowski, A.J., et al., "Isolation and Characterization of an Anti–peptide Monoclonal Antibody to Human Erythropoietin," *J. of Biol. Chem.*, 260(27): 14727–14731 (1985).

Sytkowski A.J., et al., "Immunochemical Studies of Human Erythropoietin Using Site–Specific Anti–Peptide Antibodies," *J. of Biol. Chem.*, 262(3): 1161–1165 (1987).

Wognum, A.W., et al., "Use of a Sensitive Bioimmunoabsorbent Assay to Isolate and Characterize Monoclonal Antibodies to Biologically Active Human Erythropoietin," *Blood*, 71(6): 1731–1737 (1988).

Dube, S., et al., "Glycosylation at Specific Sites of Erythropoietin is Essential for Biosynthesis, Secretion, & Biological Function," *J. of Biol. Chem.*, 263(33): 17516–17521 (1988).

Boissel, J.P., et al., "Erythropoietin Structure–Function Relationships," In *The Biology of Hematopoisis*, N. Dainiak et al., eds. (NY: Wiley–Liss, Inc.), pp. 227–232 (1990).

Yoshimura, A., et al., "Friend Spleen Focus–Forming Virus Glycoprotein gp55 Interacts With the Erythropoietin Receptor in the Endoplasmic Reticulum and Affects Receptor Metabolism," *Proc. Natl. Acad. Sci USA*, 87: 4139–4143 (1990).

Chern. J., et al., "Erythropoietin Activates the Receptor in Both Rauscher & Friend Murine Erythroleukemia Cells," *J. of Biol. Chem.*, 266(4): 2009–2012 (1991).

Watowich, S.S., et al., "Homodimerization and Constitutive Activation of the Erythropoietin Receptor," *Proc. Natl. Acad. Sci USA*, 89: 2140–2144 (1992).

Fibi, M.R., et al., "Evidence for the Location of the Receptor–Binding Site of Human Erythropoietin at the Carboxy-1–Terminal Domain," *Blood*, 77(6): 1203–1210 (1991).

Grodberg, J., et al., "Defining Human Erythropoietin Hormone Receptor Interactions by Site–Directed Mutagenesis," *Exp. Hematol.*, 20(6): 755 (Abstract 195) (Jul. 1992).

Higuchi, M., et al., "Role of Sugar Chains in the Expression of the Biological Activity of Human Erythropoietin," *J. of Biol. Chem.*, 267(11): 7703–7709 (1992).

Patel, H.R., et al., "Erythropoietin Causes Changes in Early Response Gene Expression Via Multiple Signaling Pathways: Distinct Roles for Protein Kinases & Phosphatases," *Blood*, 78(10): 304a (Abstract 1205) (Nov. 15, 1991).

Spangler, R., et al., "Erythropoietin Increases c–myc mRNA by a Protein Kinase C–dependent Pathway," *J. Biol. Chem.*, 266(2): 681–684 (1991).

(List continued on next page.)

*Primary Examiner*—David L. Fitzgerald
*Attorney, Agent, or Firm*—Hamilton, Brook, Smith & Reynolds, P.C.

[57] ABSTRACT

Provided are nucleic acids encoding erythropoietin (EPO) proteins and having modifications in the 5' and 3' noncoding sequences relative to the corresponding sequences in native EPO DNA. The invention also relates to the use of such nucleic acids to produce EPO proteins, which may have altered activity as compared to EPO proteins expressed from nucleic acids having native 5' and 3' sequences.

12 Claims, 19 Drawing Sheets

OTHER PUBLICATIONS

Chern, Y., et al, "Structural Role of Amino Acids 99–110 in Recombinant Human Erythropoietin," *Eur. J. Biochem.*, 202: 225–229 (1991).

Yamaguchi, K., et al., "Effects of Site–Directed Removal of N–Glycosylation Sites in Human Erythropoietin on Its Production & Biological Properties," *J. Biol. Chem.*, 266(30): 20434–20439 (1991).

McDonald, J.D., et al., "Cloning Sequencing and Evolutionary Analysis of the Mouse Erythropoietin Gene," *Mol. and Cell Biol.*, 6(3): 842–848 (1986).

Boissel, J–P., et al., "Erythropoietin Structure–Function Relationships. Mutant Proteins that Test a Model of Tertiary Structure," *J. Biol. Chem.* 268(21): 15983–15993 (1993).

Grodberg, J., et al., "Characterizing Arginine 103 Side Chain Contributions to Human Erythropoietin's Biological Activity by Site–Directed Mutagenesis," *Exp. Hematol.*, 21(8): (Abstract 632) (Aug. 1993).

Boissel, J.P., et al., "Erythropoietin (EPO) Structure–Function Relationships: Identification of Functionally Important Domains," *Blood* 82(10): 316a (Abstract 1250) (Nov. 15, 1993).

Powell, J.S., et al., "Human Erythropoietin Gene: High Level Expression in Stably Transfected Mammalian Cells and Chromosome Localization," *Proc. Natl. Sci. USA*, 83:6465–6469 (1986).

Tsuda, E., et al., "The Role of Carbohydrate in Recombinant Human Erythropoietin," *Eur. J. Biochem.*, 188: 405–411 (1990).

Elder, G.E., et al., "In Vitro Bioassay of Erythropoietic Activity in Serum Using Mouse Spleen Cells. The Effect of Heat Inactivation on Serum Erythropoietin," *Blood Cells*, 11: 409–416 (1986).

Endo, Y., et al., "Heat–Induced Aggregation of Recombinant Erythropoietin in the Intact and Deglycosylated States as Monitored by Gel Permeation Chromatography Combined with a Low–Angle Laser Light Scattering Technique," *J. Biochem.*, 112: 700–706 (1992).

Chern, Y., et al., "Potentiation of the Erythropoietin Response by Dimethyl Sulfoxide Priming of Erythroleukemia Cells: Evidence for Interaction of Two Signaling Pathways," *Blood*, 76(11): 2204–2209 (Dec. 1, 1990).

Yonekura, S., et al., "Erythropoietin Receptors Induced by Dimethyl Sulfoxide Exhibit Positive Cooperatively Associated with an Amplified Biologic Response," *Proc. Natl. Acad. Sci. USA*, 88: 2535–2539 (1991).

McMahon, G.F., et al., "Pharmacokinetics and Effects of Recombinant Human Erythropoietin After Intravenous and Subcutaneous Injections in Healthy Volunteers," *Blood*, 76(9): 1718–1722 (Nov. 1, 1990).

Spivak, J.L. and Hogans, B.B., "The In Vivo Metabolism of Recombinant Human Erythropoietin in the Rat," *Blood*, 73(1): 90–99 (Jan. 1989).

Showers, M., et al., "ALA Replacements Increase the Mitogenic Activity of Human Erythropoietin," *Blood*, 84(10), Suppl. 1: 369a (Abstract 1460) (Nov. 15, 1994).

Shoemaker, C.B., et al., "Murine Erythropoietin Gene: Cloning, Expression, and Human Gene Homology," *Mol. Cell. Biol.*, 6:849–858 (1986).

Cunningham et al., "High–Resolution Epitope Mapping of hGH–Receptor Interactions by Alanine–Scanning Mutagenesis," *Science* 244:1081–1085 (1989).

Boissel, J.P., et al., "Erythropoietin Structure–Function Relationships," *The Journal of Biological Chemistry*, 268:15983–15993 (1993).

R103K

R103E

R103N

R103L

HUMAN ERYTHROPOIETIN GENE                                          SEQ ID: 23

From: HOMO SAPIENS (HUMAN)
      EUKARYOTA; ANIMALIA; METAZOA; CHORDATA; VERTEBRATA; MAMMALIA;
      THERIA; EUTHERIA; PRIMATES; HAPLORHINI; CATARRHINI; HOMINIDAE.

```
              10         20         30         40         50         60
              |          |          |          |          |          |
   1   AAGCTTCTGG GCTTCCAGAC CCAGCTACTT TGCGGAACTC AGCAACCCAG GCATCTCTGA
  61   GTCTCCGCCC AAGACCGGGA TGCCCCCCAG GGGAGGTGTC CGGGAGCCCA GCCTTTCCCA
 121   GATAGCACGC TCCGCCAGTC CAAGGGTGCG CAACCGGCT GCACTCCCCT CCCGCGACCC
 181   AGGGCCCGGG AGCAGCCCCC ATGACCCACA CGCACGTCTG CAGCAGCCCC GCTCACGCCC
 241   CGGCGAGCCT CAACCCAGGC GTCCTGCCCC TGCTCTGACC CCGGGTGGCC CCTACCCCTG
 301   GCGACCCCTC ACGCACACAG CCTCTCCCCC ACCCCACCC GCGCACGCAC ACATGCAGAT
 361   AACAGCCCCG ACCCCGGCC AGAGCCGCAG AGTCCCTGGG CCACCCCGGC CGCTCGCTGC
 421   GCTGCGCCGC ACCGCGCTGT CCTCCCGGAG CCGGACCGGG GCCACCGCGC CCGCTCTGCT
 481   CCGACACCGC GCCCCTGGA CAGCCGCCCT CTCCTCTAGG CCCGTGGGGC TGGCCCTGCA
 541   CCGCCGAGCT TCCCGGGATG AGGGCCCCCG GTGTGGTCAC CCGGCGCGCC CCAGGTCGCT
 601   GAGGGACCCC GGCCAGGCGC GGAGATGGGG GTGCACGGTG AGTACTCGCG GCTGGGCGC
 661   TCCCGCCGCC CGGGTCCCTG TTTGAGCGGG GATTTAGCGC CCCGGCTATT GGCCAGGAGG
 721   TGGCTGGGTT CAAGGACCGG CGACTTGTCA AGGACCCCGG AAGGGGGAGG GGGGTGGGGC
 781   AGCCTCCACG TGCCAGCGGG GACTTGGGGG AGTCCTTGGG GATGGCAAAA ACCTGACCTG
 841   TGAAGGGGAC ACAGTTTGGG GGTTGAGGGG AAGAAGGTTT GGGGGTTCTG CTGTGCCAGT
 901   GGAGAGGAAG CTGATAAGCT GATAACCTGG GCGCTGGAGC CACCACTTAT CTGCCAGAGG
 961   GGAAGCCTCT GTCACACCAG GATTGAAGTT TGGCCGGAGA AGTGGATGCT GGTAGCTGGG
1021   GGTGGGGTGT GCACACGGCA GCAGGATTGA ATGAAGGCCA GGGAGGCAGC ACCTGAGTGC
1081   TTGCATGGTT GGGGACAGGA AGGACGAGCT GGGGCAGAGA CGTGGGGATG AAGGAAGCTG
1141   TCCTTCCACA GCCACCCTTC TCCCTCCCCG CCTGACTCTC AGCCTGGCTA TCTGTTCTAG
1201   AATGTCCTGC CTGGCTGTGG CTTCTCCTGT CCCTGCTGTC GCTCCCTCTG GCCTCCCAG
1261   TCCTGGGCGC CCCACCACGC CTCATCTGTG ACAGCCGAGT CCTGGAGAGG TACCTCTTGG
1321   AGGCCAAGGA GGCCGAGAAT ATCACGGTGA CCCCTTCC CCAGCACATT CCACAGAACT
```

FIGURE 8A

```
1381  CACGCTCAGG GCTTCAGGGA ACTCCTCCCA GATCCAGGAA CCTGGCACTT GGTTTGGGGT

1411  GGAGTTGGGA AGCTAGACAC TGCCCCCCTA CATAAGAATA AGTCTGGTGG CCCCAAACCA

1501  TACCTGGAAA CTAGGCAAGG AGCAAAGCCA GCAGATCCTA CGGCCTGTGG GCCAGGGCCA

1561  GAGCCTTCAG GGACCCTTGA CTCCCGGGC TGTGTGCATT TCAGACGGGC TGTGCTGAAC

1621  ACTGCAGCTT GAATGAGAAT ATCACTGTCC CAGACACCAA AGTTAATTTC TATGCCTGGA

1681  AGAGGATGGA GGTGAGTTCC TTTTTTTTTT TTTTTCCTTT CTTTTGGAGA ATCTCATTTG

1741  CGAGCCTGAT TTTGGATGAA AGGGAGAATG ATCGGGGAA AGGTAAAATG GAGCAGCAGA

1801  GATGAGGCTG CCTGGGCGCA GAGGCTCACG TCTATAATCC CAGGCTGAGA TGGCCGAGAT

1861  GGGAGAATTG CTTGAGCCCT GGAGTTTCAG ACCAACCTAG GCAGCATAGT GAGATCCCCC

1921  ATCTCTACAA ACATTTAAAA AAATTAGTCA GGTGAAGTGG TGCATGGTGG TAGTCCCAGA

1981  TATTTGGAAG GCTGAGGCGG GAGGATCGCT TGAGCCCAGG AATTTGAGGC TGCAGTGAGC

2041  TGTGATCACA CCACTGCACT CCAGCCTCAG TGACAGAGTG AGGCCCTGTC TCAAAAAAGA

2101  AAAGAAAAAA GAAAAATAAT GAGGGCTGTA TGGAATACAT TCATTATTCA TTCACTCACT

2161  CACTCACTCA TTCATTCATT CATTCATTCA ACAAGTCTTA TTGCATACCT TCTGTTTGCT

2221  CAGCTTGGTG CTTGGGGCTG CTGAGGGGCA GGAGGGAGAG GGTGACATGG GTCAGCTGAC

2281  TCCCAGAGTC CACTCCCGTG AGGTCGGGCA GCAGGCCGTA GAAGTCTGGC AGGGCCTGGC

2341  CCTGCTGTCG GAAGCTGTCC TGCGGGGCCA GGCCCTGTTG GTCAACTCTT CCCAGCCGTG

2401  GGAGCCCCTG CAGCTGCATG TGGATAAAGC CGTCAGTGGC CTTCGCAGCC TCACCACTCT

2461  GCTTCGGGCT CTGGGAGCCC AGGTGAGTAG GAGCGGACAC TTCTGCTTGC CCTTTCTGTA

2521  AGAAGGGGAG AAGGGTCTTG CTAAGGAGTA CAGGAACTGT CCGTATTCCT TCCCTTTCTG

2581  TGGCACTGCA GCGACCTCCT GTTTTCTCCT TGGCAGAAGG AAGCCATCTC CCCTCCAGAT

2641  GCGGCCTCAG CTGCTCCACT CCGAACAATC ACTGCTGACA CTTTCCGCAA ACTCTTCCGA

2701  GTCTACTCCA ATTTCCTCCG GGGAAAGCTG AAGCTGTACA CAGGGGAGGC CTGCAGGACA

2761  GGGGACAGAT GACCAGGTGT GTCCACCTGG GCATATCCAC CACCTCCCTC ACCAACATTG

2821  CTTGTGCCAC ACCCTCCCCC GCCACTCCTG AACCCGTCG AGGGGCTCTC AGCTCAGCGC

2881  CAGCCTGTCC CATGGACACT CCAGTGCCAG CAATGACATC TCAGGGCCA GAGGAACTGT

2941  CCAGAGAGCA ACTCTGAGAT CTAAGGATGT CACAGGGCCA ACTTGAGGGC CCAGAGCAGG
```

FIGURE 8B

```
3001  AAGCATTCAG AGAGCAGCTT TAAACTCAGG GACAGAGCCA TGCTGGGAAG ACGCCTGAGC

3061  TCACTCGGCA CCCTGCAAAA TTTGATGCCA GGACACGCTT TGGAGGCGAT TTACCTGTTT

3121  TCGCACCTAC CATCAGGGAC AGGATGACCT GGAGAACTTA GGTGGCAAGC TGTGACTTCT

3181  CCAGGTCTCA CGGGCATGGG CACTCCCTTG GTGGCAAGAG CCCCCTTGAC ACCGGGGTGG

3241  TGGGAACCAT GAAGACAGGA TGGGGCTGG  CCTCTGGCTC TCATGGGGTC CAAGTTTTGT

3301  GTATTCTTCA ACCTCATTGA CAAGAACTGA AACCACCAAT ATGACTCTTG GCTTTTCTGT

3361  TTTCTGGGAA CCTCCAAATC CCCTGGCTCT GTCCCACTCC TGGCAGCAGT GCAGCAGGTC

3421  CAGGTCCGGG AAATGAGGGG TGGAGGGGGC TGGGCCCTAC GTGCTGTCTC ACACAGCCTG

3481  TCTGACCTCT CGACCTACCG GCCTAGGCCA CAAGCTCTGC CTACGCTGGT CAATAAGGTG

3541  TCTCCATTCA AGGCCTCACC GCAGTAAGGC AGCTGCCAAC CCTGCCCAGG GCAAGGCTGC

```
            10         20         30         40         50         60
             |          |          |          |          |          |
   1    CCACCCCGGC CGCTCGCTGC GCTGCGCCGC ACCGCGCTGT CCTCCCGGAG CCGGACCGGG

61    GCCACCGCGC CCGCTCTGCT CCGACACCGC GCCCCCTGGA CAGCCGCCCT CTCCTCTAGG

121    CCCGTGGGGC TGGCCCTGCA CCGCCGAGCT TCCCGGGATG AGGGCCCCCG GTGTGGTCAC

181    CCGGCGCGCC CCAGGTCGCT GAGGGACCCC GGCCAGGCGC GGAG
```

Total number of bases is: 224.                FIGURE 9A

```
            10         20         30         40         50         60
             |          |          |          |          |          |
   1    CCACCCCGGC CGCTCGCTGC GCTGCGCCGC ACCGCGCTGT CCTCCCGGAG CCGGACCGGG

61    GCCACCGCGC CCGCTCTGCT CCGACACCGC GCCCCCTGGA TCCCGGGATG AGGGCCCCCG

121    GTGTGGTCAC CCGGCGCGCC CCAGGTCGCT GAGGGACCCC GGCCAGGCGC GGAG
```

Total number of bases is: 174                 FIGURE 9B

```
            10         20         30         40         50         60
             |          |          |          |          |          |
   1    CCACCCCGGC CGCTCGCTGC GCTGCGCCGC ACCGCGCTGT CCTCCCGGAG CCGGACCGGG

61    GCCACCGCGC CCGCTCTGCT CCGACACCGC GCCCCCTGGA CAGCCGCCCT CTCCTCTAGG

121    CCCGTGGGGC TGGCCCTGCA CCGCCGAGCT GAGGGACCCC GGCCAGGCGC GGAG
```

Total number of bases is: 174                 FIGURE 9C

```
            10         20         30         40         50         60
             |          |          |          |          |          |
   1    CAGCCGCCCT CTCCTCTAGG CCCGTGGGGC TGGCCCTGCA CCGCCGAGCT TCCCGGGATG

61    AGGGCCCCCG GTGTGGTCAC CCGGCGCGCC CCAGGTCGCT GAGGGACCCC GGCCAGGCGC

121    GGAG
```

Total number of bases is: 124                 FIGURE 9D

```
            10         20         30         40         50         60
             |          |          |          |          |          |
   1    TCCCGGGATG AGGGCCCCCG GTGTGGTCAC CCGGCGCGCC CCAGGTCGCT GAGGGACCCC

61    GGCCAGGCGC GGAG
```

Total number of bases is: 74                  FIGURE 9E

```
            10         20         30         40         50         60
             |          |          |          |          |          |
   1    CCAGGTCGCT GAGGGACCCC GGCCAGGCGC GGAG
```

Total number of bases is: 34                  FIGURE 9F

```
           10         20         30         40         50         60
            |          |          |          |          |          |
1     CCAGGTGTGT CCACCTGGGC ATATCCACCA CCTCCCTCAC CAACATTGCT TGTGCCACAC

61    CCTCCCCCGC CACTCCTGAA CCCCGTCGAG GGGCTCTCAG CTCAGCGCCA GCCTGTCCCA

121   TGGACACTCC AGTGCCAGCA ATGACATCTC AGGGGCCAGA GGAACTGTCC AGAGAGCAAC

181   TCTGAGATCT AAGGATGTCA
```

Total number of bases is: 200                    FIGURE 10A

```
           10         20         30         40         50         60
            |          |          |          |          |          |
1     CCAGGTGTGT CCACCTGGGC ATATCCACCA CCTCCCTCAC CCACATTGCT TGTGCCACAC

61    CCTCCCCCGC CACTCCTGAA CCCCGTCGAG GGGCTCTCAG CTCAGCGCCA GCCTGTCCCA

121   TGGACACTCC AGTGCCAGCA ATGACATCTC
```

Total number of bases is: 150                    FIGURE 10B

```
           10         20         30         40         50         60
            |          |          |          |          |          |
1     CCAGGTGTGT CCACCTGGGC ATATCCACCA CCTCCCTCAC CAACATTGCT TGTGCCACAC

61    CCTCCCCCGC CACTCCTGAA CCCCGTCGAG GGGCTCTCAG
```

Total number of bases is: 100                    FIGURE 10C

```
           10         20         30         40         50         60
            |          |          |          |          |          |
1     CCAGGTGTGT CCACCTGGGC ATATCCACCA CCTCCCTCAC CAACATTGCT
```

Total number of bases is: 50                     FIGURE 10D

```
           10         20         30         40         50         60
            |          |          |          |          |          |
1     CCAGGTGTGT CCACCTGGGC ATATCCACCC AGTGCCAGCA ATGACATCTC AGGGGCCAGA

61    GGAACTGTCC AGAGAGCAAC TCTGAGATCT AAGGATGTCA
```

Total number of bases is: 100                    FIGURE 10E

… 6,153,407

ERYTHROPOIETIN DNA HAVING MODIFIED 5' AND 3' SEQUENCES AND ITS USE TO PREPARE EPO THERAPEUTICS

RELATED APPLICATIONS

This application is a continuation-in-part application of U.S. Ser. No. 08/808,881 which was filed on Feb. 28, 1997, which is a divisional of U.S. Ser. No. 08/383,743 filed Feb. 2, 1995, issued as U.S. Pat. No. 5,614,184 on Mar. 25, 1997, which is a continuation-in-part application of U.S. Ser. No. 08/113,080, filed Aug. 26, 1993, now abandoned, which is a continuation-in-part application of U.S. Ser. No. 07/920,810, filed Jul. 28, 1992, now abandoned. The teachings of these related applications are incorporated herein by reference.

GOVERNMENT SUPPORT

The invention described herein was supported in whole or in part by Grant No. 38841 from the National Institutes of Health and Grant No. N00014-90-1847 from the U.S. Navy. The U.S. Government has certain rights in the invention.

BACKGROUND OF THE INVENTION

The glycoprotein hormone erythropoietin regulates the growth and differentiation of red blood cell (erythrocyte) progenitors. The hormone is produced in the fetal liver and adult kidney. Erythropoietin induces proliferation and differentiation of red blood cell progenitors through interaction with receptors on the surface of erythroid precursor cells.

Several approaches have been employed to identify those features of the protein that are relevant to its structure and function. Examination of the homologies among the amino acid sequences of erythropoietin proteins of various species has demonstrated several highly conserved regions (McDonald, J. D., et al., *Mol. Cell. Biol.* 6: 842–848 (1986)).

Oligonucleotide-directed mutagenesis has been used to prepare structural mutants of erythropoietin, lacking specific sites for glycosylation. Studies indicate that N-linked carbohydrates are important for proper biosynthesis and/or secretion of erythropoietin. These studies also show that glycosylation is important for in vivo, but not in vitro, biological activity. (Dube, S., et al., *J. Biol. Chem.* 263:17516–17521 (1988); Yamaguchi, K., et al., *J. Biol. Chem.* 266:20434–20439 (1991); Higuchi, M., et al., *J. Biol. Chem.* 267:7703–7709 (1992)).

Studies with monoclonal anti-peptide antibodies have shown that the amino terminus and the carboxy-terminal region (amino acids 152–166) of erythropoietin may be involved with biological activity. It has also been demonstrated that antibodies to amino acids 99–119 and 111–129 block the hormone's biological activity, apparently by binding to two distinct non-overlapping domains (99–110 and 120–129). (Sytkowski, A. J. and Donahue, K. A., *J. Biol. Chem.* 262:1161–1165 (1987)). Thus, it was hypothesized that amino acids 99–129 were important in the formation of a functional region involved in receptor recognition, either through forming a necessary component of the protein's tertiary structure or through direct participation in receptor binding, or both.

Preliminary experiments suggested that alterations in localized secondary structure within the 99–129 region resulted in inactivation of erythropoietin. Therefore, a possible structural role for amino acids 99–129 has been postulated. Recently, a series of experiments indicated that amino acids 99–110 (Domain 1) play a critical role in establishing the biologically active conformation of human erythropoietin. (Chern, Y., et al., *Eur. J. Biochem.* 202:225–229 (1991)).

These Domain 1 mutants, in which a group of three amino acids was deleted and replaced by two different amino acids, were found to be biologically inactive. Furthermore, these mutations in Domain 1 inhibited the secretion of the mutant erythropoietin into cell culture medium. (Chern, Y., et al., *Eur. J. Biochem.* 202:225–229 (1991)). Inhibition of secretion in mammalian cells is consistent with a profound structural change of the polypeptide hormone. Profound structural changes could significantly affect the ability of the hormone to interact with its cognate receptor. Thus, these mutant erythropoietin polypeptides are not suitable for elucidating the structure/function relationship that exists between erythropoietin and its cellular receptor. Nor are these mutants suitable erythropoietin antagonists for use, for example, in therapeutic treatment of polycythemias, or over production of erythropoietin. Thus, it would be beneficial to precisely determine which amino acids are critical to the erythropoietin polypeptide to maintain a stable, biologically active conformation which retains its secretable properties and its ability to bind to the erythropoietin receptor.

Moreover, the precise determination of critical amino acid residues would be useful to alter the biological activity of erythropoietin, either decreasing or increasing one or more biological properties of the protein.

SUMMARY OF THE INVENTION

The present invention relates to isolated DNA encoding mutated erythropoietin proteins which have altered biological activity, yet retain their secretable properties (i.e., secretable erythropoietin proteins).

In one embodiment, the present invention relates to isolated DNA encoding secretable erythropoietin proteins which have at least one amino acid residue in Domain 1 which differs from the amino acid residue present in the corresponding position of wildtype erythropoietin and which have altered ability to regulate the growth and differentiation of red blood cell progenitors. Domain 1 of the mutants described herein refers to the amino acids which correspond to amino acids 99–110 (SEQ ID NO: 1) of the wildtype recombinant erythropoietin. Altered ability is defined as ability different from that of the wildtype recombinant erythropoietin ability to regulate the growth and differentiation of red blood cell progenitors. As used herein, altered ability to regulate the growth and differentiation of red blood cell progenitor cells refers to biological activity different from wildtype recombinant erythropoietin activity (i.e., altered biological activity relative to wildtype recombinant erythropoietin activity). The mutated erythropoietin proteins of the present invention can be secreted in homologous and heterologous expression systems. For example, the mutated erythropoietin proteins of the present invention can be secreted in mammalian, bacterial or yeast expression systems.

The present invention also relates to the modified secretable mutant erythropoietin proteins encoded by the isolated DNA described above. These modified secretable erythropoietin proteins have altered biological activities. For example, the modified secretable mutant erythropoietin may have decreased ability relative to wildtype erythropoietin protein to regulate growth and differentiation of red blood cell progenitor cells. As used herein, decreased ability to regulate growth and differentiation of red blood cell progenitor cells is also referred to as decreased biological activity relative to wildtype erythropoietin activity. Wildtype erythropoietin activity is also referred to herein as biological activity of wildtype erythropoietin. Alternately, a modified secretable mutant erythropoietin protein described herein may exhibit increased heat stability relative to wildtype erythropoietin protein.

The modified erythropoietin proteins described herein comprise an amino acid sequence with at least one amino acid residue different from the amino acid residue present at the corresponding position in Domain 1 in the wildtype erythropoietin. These erythropoietin proteins are referred to as modified secretable human recombinant erythropoietin proteins having altered ability (i.e., decreasing or enhancing ability) relative to wildtype erythropoietin protein to regulate the growth and differentiation of red blood cell progenitors.

The term modified, as used herein, includes substitution of a different amino acid residue, or residues, as well as deletion or addition of an amino acid residue, or residues.

Until the present invention, mutations within the erythropoietin sequence which result in the alteration of biological activity have also frequently resulted in a concurrent loss of secretability of the protein from transfected cells. This loss of secretability is consistent with a loss of structural integrity. (Boissel, J-P. and Bunn, H. F., "The Biology of Hematopoiesis", pp. 227–232, John Wiley and Sons, New York (1989)). Now, the sites critical to the maintenance of a stable, biologically active conformation have been identified by means of oligonucleotide-directed mutagenesis and have been found to occur in Domain 1 (amino acids 99–110) (SEQ ID NO: 1) of human recombinant erythropoietin. Modifications of the wildtype erythropoietin have been made and the encoded erythropoietin proteins have been expressed. The resulting mutant erythropoietin proteins described herein have altered erythropoietin regulating activity, as demonstrated in the art-recognized bioassay of Krystal, G., Exp. Hematol. 11:649–660 (1983). Activity of the resulting erythropoietin proteins has also been evaluated by commercially available radioimmunoassay protocols.

In particular, the arginine 103 site is essential for erythropoietin activity. As shown herein, replacement of the arginine 103 by another amino acid results in a modified erythropoietin with significantly decreased biological activity relative to wildtype erythropoietin activity. Modifications at this site, as well as other sites within Domain 1, can similarly be made to enhance regulating activity, as well as to decrease, or reduce regulating ability.

In another embodiment, the present invention relates to mutant proteins described herein that comprise modified erythropoietin proteins produced by alterations in the 5' and/or 3' noncoding regions of the wildtype gene in addition to mutations in coding regions. Hereinafter, the term modified erythropoietin variant protein will be used to describe these molecules.

These recombinant variant proteins can have altered biological activity. Altered biological activity is defined herein as activity different from that of the wildtype or recombinant protein (e.g., the activity of modified erythropoietin variant proteins to regulate the growth and differentiation of red blood cell progenitors). Modified erythropoietin variant proteins can have increased activity relative to wildtype erythropoietin to regulate growth and differentiation of red blood cell progenitor cells. Alternatively, the erythropoietin variant proteins can have decreased biological activity relative to the wildtype erythropoietin.

Mutations in noncoding regions of the gene (e.g., 5' untranslated regions or UTR) can lead to differences in RNA translation as described, e.g., in Schultz, D. E., et al., J. Virol. 70:1041–1049, 1996; Kozak, M., J. Mol. Biol. 235:95–110, 1994; and Kozak, M., J. Biol. Chem. 266:19867–19870, 1991. For example, as described in detail in Example 4, computer modeling can be used to predict differences in RNA secondary structure (e.g., free energy of loops and base pairs) following nucleotide alterations in 3' and 5' UTR of the erythropoietin gene. Although secondary structure changes in EPO RNA, following mutations in the 5' or 3' UTR, are used as the specific example, it is understood that the instant invention described herein can be used to produce any suitable polypeptide variant protein. As used herein, the term mutation refers to any alteration in the nucleic acid sequence encoding a polypeptide (e.g., a point mutation; the addition, deletion and/or substitution of one or more nucleotides).

Secondary structure has been shown to be a critical component in determining the rates of translation efficiency of several proteins (Bettany, A. J., et al., J. Biol. Chem. 267:16531–16537, 1992; Kozak, M., J. Mol. Biol. 235:95–110, 1994). By implication, altered rates of translation may affect posttranslational modifications, for example, glycosylation patterns, and, thus, proper folding of the resulting protein leading to changes in the chemistry, structure and function of the protein. The modified erythropoietin variant proteins described herein are unique in that they are composed of mutant proteins produced by alterations in 5' and 3' untranslated (noncoding) regions of the gene.

The modified secretable erythropoietin proteins described herein provide useful reagents to further elucidate the structure/function relationship of erythropoietin and its cellular receptor.

Such modified secretable erythropoietin proteins with altered regulating ability can also be used for therapeutic purposes. For example, modified erythropoietin proteins with enhanced biological activity would be a more potent therapeutic, therefore requiring a lower effective dose or less frequent administration to an individual. Erythropoietin proteins with decreased biological activity that still retain their structural integrity and bind to their cognate receptor would be useful to decrease growth and differentiation of red blood cell precursors in certain leukemias and polycythemias. Furthermore, an erythropoietin protein that selectively triggers only certain events within the red blood cell precursor cell would be useful in treating various hematological conditions.

Further, it is expected that modified secretable mutant erythropoietin proteins with increased heat stability relative to wildtype erythropoietin proteins would have a longer plasma half-life relative to wildtype erythropoietin proteins. Thus, such modified erythropoietin proteins with increased heat stability can be useful therapeutically. For example, modified secretable mutant erythropoietin proteins with increased heat stability would be especially important in patients with a fever and/or experiencing an increased metabolic state.

The present invention also relates to methods of modifying or altering the regulating activity of a secretable erythropoietin protein.

This invention further relates to pharmaceutical compositions comprising an effective amount of modified secretable human recombinant erythropoietin in a physiologically acceptable carrier.

The present invention also relates to a method of evaluating a substance for ability to regulate growth and differentiation of red blood cell progenitor cells.

BRIEF DESCRIPTION OF THE DRAWINGS

FIG. 6A shows the activity of R103A. FIG. 6B shows the activity of R103D. FIG. 6C shows the activity of R103K. FIG. 6D shows the activity of R103E. FIG. 6E shows the activity of R103N. FIG. 6F shows the activity of R103Q. FIG. 6G shows the activity of R103H. FIG. 6H shows the activity of R103L.

FIGS. 8A–C depict the nucleotide sequence of the human erythropoietin gene (SEQ ID NO:23).

FIGS. 9A–F depict the nucleic acid sequence of nucleotides 401–624 in the 5' untranslated region of the EPO gene (SEQ ID NO:24)(FIG. 9A) and five variant sequences (SEQ ID NOS: 25–29)(FIGS. 9B–9F).

FIGS. 10A–10E depict the nucleic acid sequence of nucleotides 2773–2972 in the 3' untranslated region of the EPO gene (SEQ ID NO:30)(FIG. 10A) and four variant sequences in that region (SEQ ID NOS: 31–34)(FIGS. 10B–10E).

DETAILED DESCRIPTION OF THE INVENTION

Figure 1:
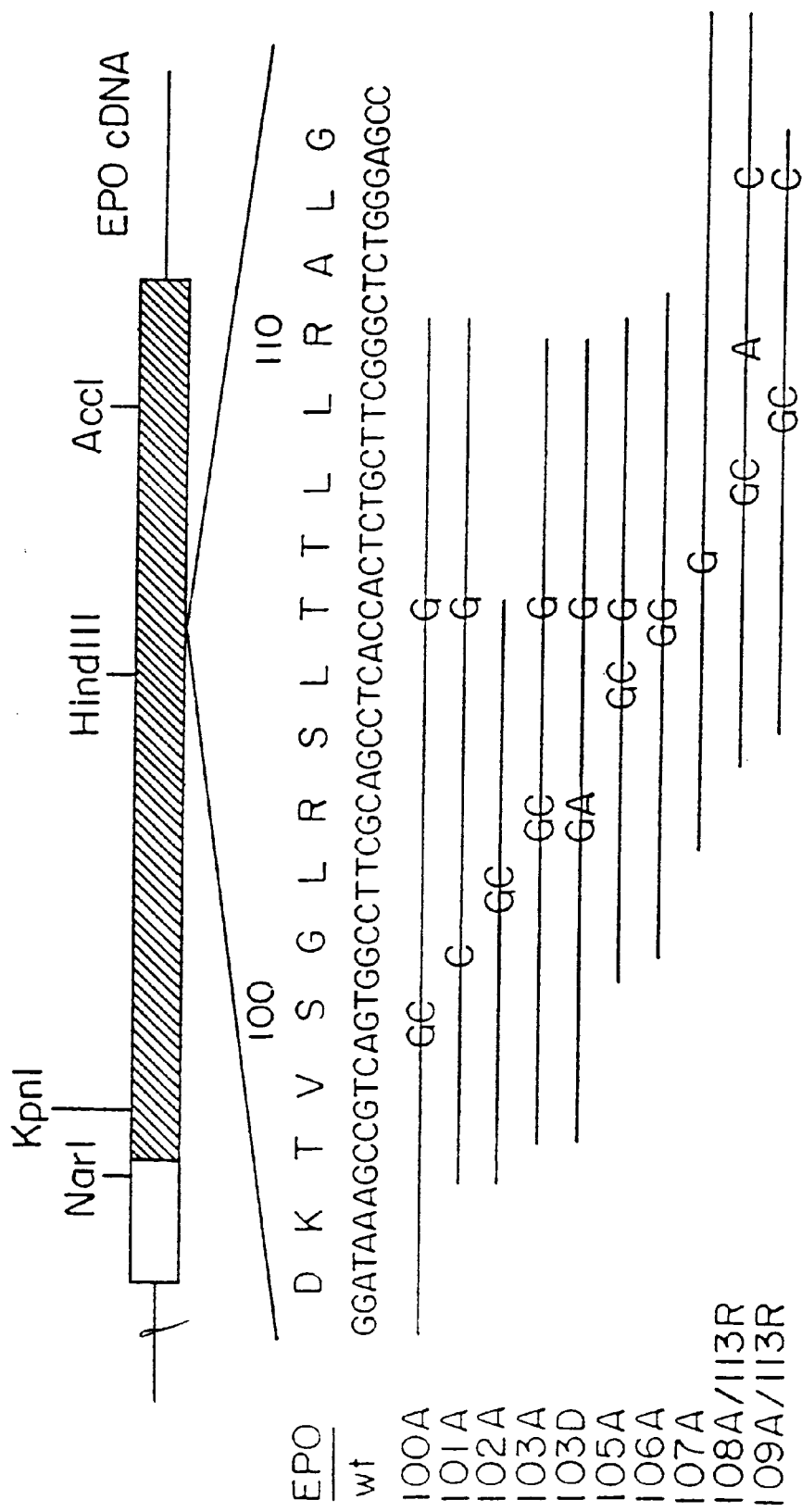
FIG. 1 is a schematic diagram of the in vitro mutagenesis protocol. WT=wildtype erythropoietin.

The present invention is based on the identification of amino acid residues of the erythropoietin polypeptide which are critical for its biological activity and secretable properties. These sites have been precisely defined through oligonucleotide-directed mutagenesis and used to create mutant human recombinant erythropoietin proteins which are altered by one, or more, amino acid substitutions and thus differ from wildtype erythropoietin.

The term "recombinant", as used herein, means that a host protein is derived from recombinant (e.g., eukaryotic or prokaryotic host cell) expression systems which include, for example, yeast (e.g., Saccharomyces), bacteria (such as, Escherichia or Bacillus), and animal cells including insect or mammalian expression systems. Proteins expressed in most bacterial cultures will be free of glycan. Protein expressed in yeast may have a glycosylation pattern different from protein expressed in mammalian cells.

As used herein, the term nucleotide sequence or nucleic acid sequence refers to a heteropolymer of deoxyribonucleotides (DNA) or ribonucleotides (RNA).

Nucleic acid sequences encoding the proteins provided in this invention can be assembled from DNA, either cDNA or genomic DNA, or RNA, and short oligonucleotide linkers to provide a synthetic nucleic acid sequence which is capable of being expressed in a recombinant transcriptional unit.

Homologous nucleic acids, including DNA or RNA, can be detected and/or isolated by hybridization (e.g., under high stringency conditions or moderate stringency conditions). "Stringency conditions" for hybridization is a term of art which refers to the conditions of temperature and buffer concentration which permit hybridization of a particular nucleic acid to a second nucleic acid in which the first nucleic acid may be perfectly complementary to the second, or the first and second may share some degree of complementarity which is less than perfect. For example, certain high stringency conditions can be used which distinguish perfectly complementary nucleic acids from those of less complementarity. "High stringency conditions" and "moderate stringency conditions" for nucleic acid hybridizations are explained in several technical protocol reference texts, for example, Ausubel, F. M., et al., "Current Protocols in Molecular Biology" (1995), the teachings of which are hereby incorporated by reference. The exact conditions which determine the stringency of hybridization depend not only on ionic strength, temperature and the concentration of destabilizing agents such as formamide, but also on factors such as the length of the nucleic acid sequence, base composition, percent mismatch between hybridizing sequences and the frequency of occurrence of subsets of that sequence within other non-identical sequences. Thus, high or moderate stringency conditions could be determined for detecting the various forms of recombinant erythropoietin.

By varying hybridization conditions from a level of stringency at which no hybridization occurs to a level at which hybridization is first observed, conditions which will allow a given sequence to hybridize (e.g., selectively) with the most similar sequences in the sample can be determined.

Exemplary conditions are described in Krause, M. H. and Aaronson, S. A., Methods in Enzymology, 200:546–556, 1991. Also, "Current Protocols in Molecular Biology" (supra), which describes how to determine washing conditions for moderate or low stringency conditions. Washing is the step in which conditions are usually set so as to determine a minimum level of complementarity of the hybrids. Generally, starting from the lowest temperature at which only homologous hybridization occurs, each ° C. by which the final wash temperature is reduced (holding SSC concentration constant) allows an increase by 1% in the maximum extent of mismatching among the sequences that hybridize. Generally, doubling the concentration of SSC results in an increase in $T_m$ of –17° C. Using these guidelines, the washing temperature can be determined for high, moderate or low stringency, depending on the level of mismatch sought. For example, in this invention alterations in the noncoding regions of the gene (5' and 3' untranslated regions) may necessitate changes in stringency conditions from low to medium to high depending upon the number of nucleotides that are modified that differ from the condition used to detect wild type versions of the gene. Where appropriate the salt concentrations and temperatures will be adjusted accordingly.

IDENTIFICATION OF AMINO ACID RESIDUES OF HUMAN RECOMBINANT ERYTHROPOIETIN CRITICAL FOR BIOLOGICAL ACTIVITY

Previously, anti-peptide antibodies to several hydrophilic domains of the erythropoietin molecule had demonstrated that antibodies to amino acids 99–110 (Domain 1) and 111–129 (Domain 2) block the hormone's biological activity. Binding of the antibody to a portion of the erythropoietin molecule that participated in receptor recognition would block such recognition, thereby neutralizing erythropoietin's biological activity. (Sytkowski, A. J. and Donahue, K. A., J. Biol. Chem. 262:1161–1165 (1987)).

A series of mutants across the 99–129 region was produced by sequentially replacing three amino acids with Glu-Phe. Mutations in amino acid residues 99–110 caused a profound structural change which inhibited secretion of the mutant erythropoietin after biosynthesis. (Chern, Y., et al., *Eur. J. Biochem.* 202:225–229 (1991)). To precisely identify the amino acid site, or sites, critical for receptor recognition and biological activity, amino acids 100–109 were studied by alanine scanning mutagenesis, as described in detail in Example 1.

Briefly, human recombinant erythropoietin cDNA (Powell, J. W., et al., *Proc. Natl. Acad. Sci. USA* 83:6465–6469 (1986)) was inserted into the Phagemid vector pSELECT (Promega Corp., Madison, Wis.) which contains two genes for antibiotic resistance. One of these genes, specific for tetracycline resistance is always functional, while the other, specific for ampicillin resistance, has been inactivated. The single-stranded template for the mutagenesis reaction was prepared by growing cultures of bacteria transformed with the Phagemid and infected with a helper phage. The resulting single-stranded DNA was isolated.

Two oligonucleotides were annealed to this recombinant ssDNA template. The first oligonucleotide was an ampicillin repair oligo designed to convert the vector to ampicillin resistance and the second oligonucleotide was a mutagenic oligo designed to change a portion of the erythropoietin cDNA sequence.

Subsequently, the mutant second strand was synthesized in vitro using T4 DNA polymerase and ligated. This DNA was then transformed into a repair minus strain of *E. coli* and these cells were grown in the presence of ampicillin. The phagemid was then harvested and a second round of transformation was carried out and mutants were selected on ampicillin plates. This resulted in the production of a double stranded phagemid containing both the ampicillin resistance gene and the mutated erythropoietin cDNA.

FIG. 1 shows the region of the erythropoietin cDNA encoding amino acids 96–113 (SEQ ID NO: 2) and the corresponding wildtype erythropoietin DNA sequence encoding amino acids 96–113 (SEQ ID NO: 3). The column of numbers on the left hand side of FIG. 1 indicates the amino acid substitution. The only amino acid residue substitutions made were as indicated. The remainder of the human recombinant erythropoietin DNA sequence was not altered. (The remaining, unaltered human recombinant DNA sequence is not shown.) Thus, for example, 100A (SEQ ID NO: 4) indicates that amino acid 100, normally a serine residue, was replaced by alanine, 101A (SEQ ID NO: 5) indicates that glycine 101 was replaced by alanine, and so forth (SEQ ID NOS: 6–16).

Some sites were mutated more than once. For example, amino acid 103 was mutated twice. The first mutation was the substitution of alanine for arginine 103 (SEQ ID NO: 7) and the second substitution was aspartic acid for arginine (SEQ ID NO: 8).

Two double mutants were also produced, 108A/113R (SEQ ID NO: 12) and 109A/113R (SEQ ID NO: 13). In these two instances, amino acids 108 and 109 were each substituted with alanine in the second mutation and the replacement of glycine 113 with arginine was introduced. The changes in nucleotide sequence in each mutagenic oligo are indicated in FIG. 1 and Table I (SEQ ID NOS: 4–22). In Table I, the underlined nucleotides are those which differ from the wildtype erythropoietin sequence. A silent mutation designed to introduce a restriction site, Hinf I, allowing convenient initial screening for mutated erythropoietin cDNAs, was also introduced.

In addition, two mutants in the region of the erythropoietin cDNA encoding amino acids 1–26 (the amino-terminus region) were produced. In these two instances, amino acid 14, normally an arginine, was replaced either by alanine (14A) or aspartic acid (14D).

Figure 2:
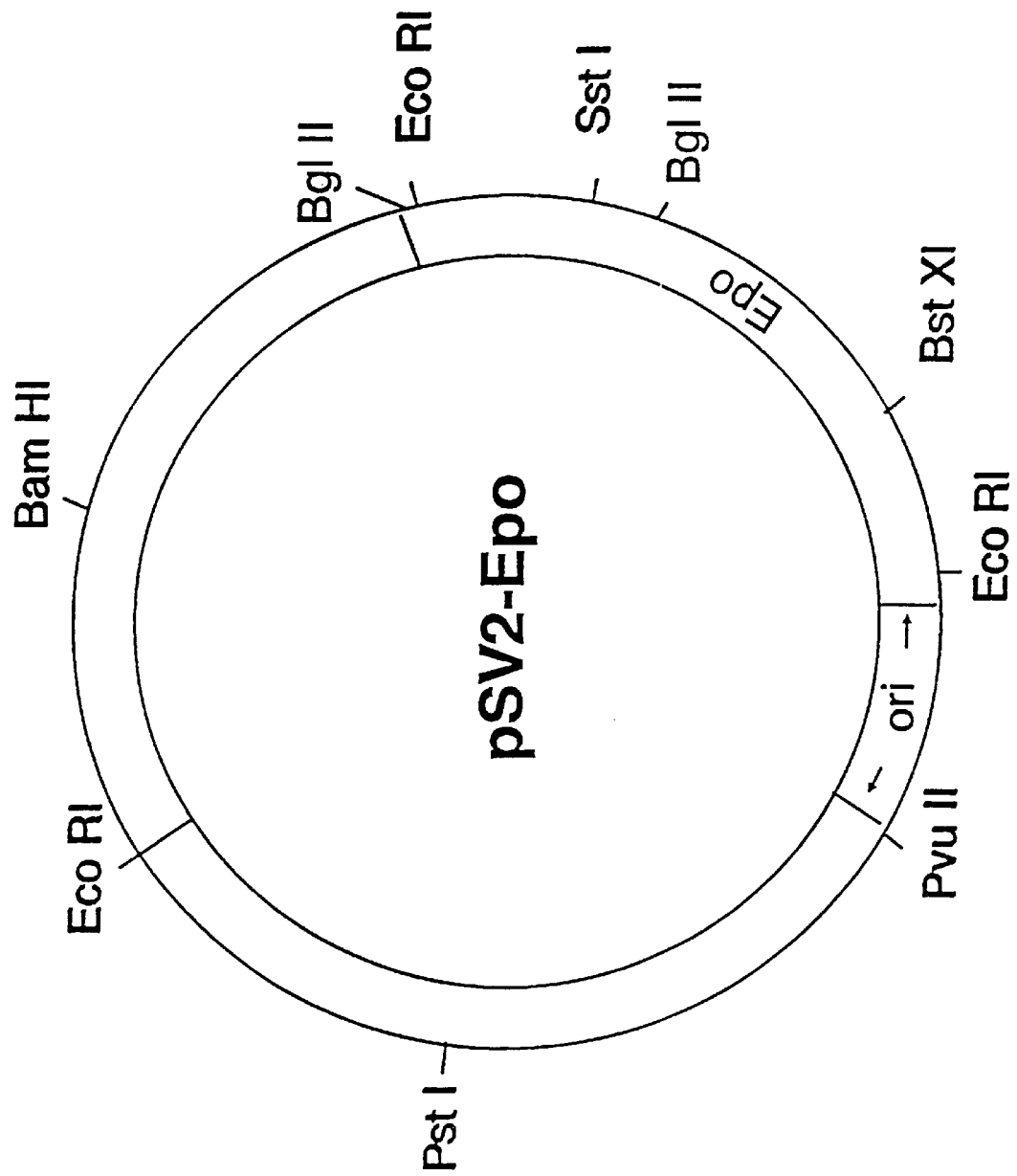
FIG. 2 depicts the structure of expression vector pSV-2-erythropoietin.

Each mutated erythropoietin cDNA was identified by restriction analysis, using standard laboratory protocols, and its structure was confirmed by DNA sequencing. The mutated erythropoietin cDNA was then inserted into the expression vector pSV-2 (FIG. 2) using standard laboratory techniques. (Mulligan, R. C., et al. *Nature* 277:108–114 (1979); Sambrook, et al., "*Molecular Cloning: A Laboratory Manual*", (1989)).

As described in detail in Example 2, COS-7 cells were transfected with the pSV-2-erythropoietin constructs. After three days, the supernatant medium was harvested and the biological activity of the mutant erythropoietin proteins and wildtype erythropoietin was measured by the Krystal bioassay (Krystal, G., *Exp. Hematol.* 11:649–660 (1983)). Briefly, the bioassay of Krystal measures the ffect of erythropoietin on intact mouse spleen cells. Mice were treated with phenylhydrazine to stimulate production of erythropoietin-responsive red blood cell progenitor cells. After treatment, the spleens were removed, intact spleen cells were carefully isolated and incubated with various amounts of wildtype erythropoietin or the mutant erythropoietin proteins described herein. After an overnight incubation, $^3$H thymidine was added and its incorporation into cellular DNA was measured. The amount of $^3$H thymidine incorporation is indicative of erythropoietin-stimulated production of red blood cells via interaction of erythropoietin with its cellular receptor. The concentration of mutant erythropoietin protein, as well as the concentration of wildtype erythropoietin, was quantified by competitive radioimmunoassay (Incstar, Stillwater, Minn.). Specific activities were calculated as international units measured in the Krystal bioassay divided by micrograms as measured as immunoprecipitable protein by RIA. Both assays used wildtype recombinant human erythropoietin standardized against the World Health Organization Second International Reference Standard preparation.

Figure 3:
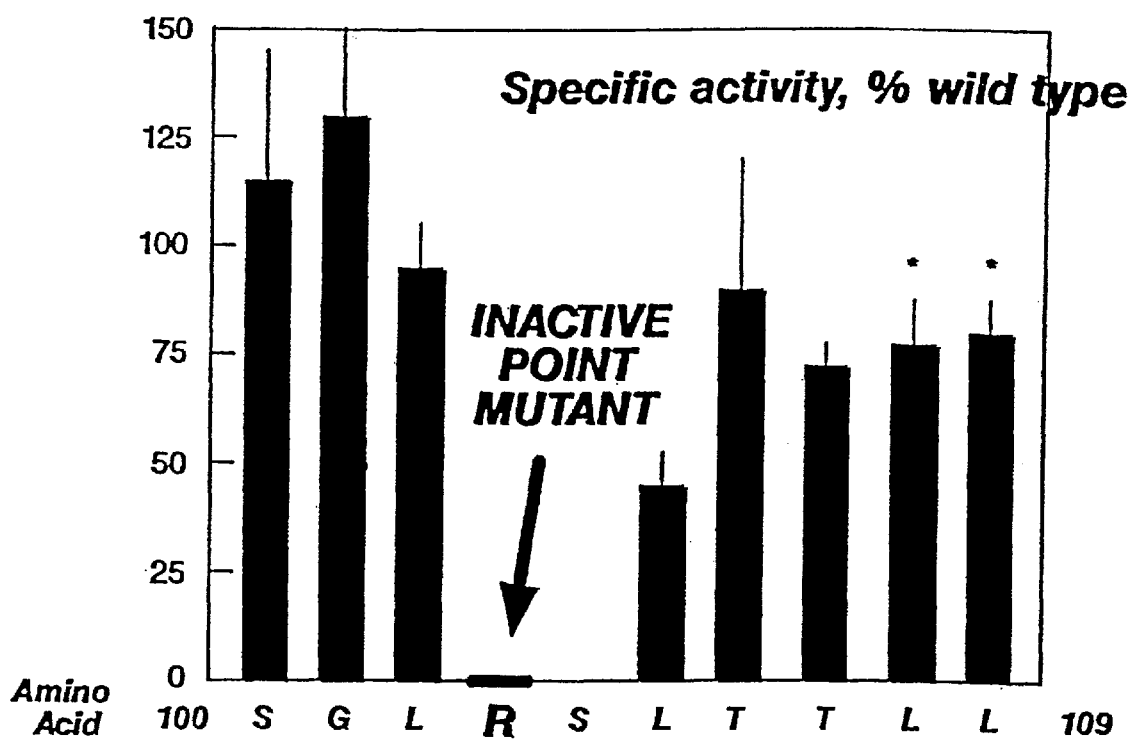
FIG. 3 is a graphic representation of the specific activities of nine mutant erythropoietin proteins.

Two sets of experiments were performed in order to determine the specific biological activities of these mutant erythropoietin proteins. Specific activities of nine of the mutant erythropoietin proteins (SEQ ID NOS: 4–13) assayed in the first set of experiments are shown in FIG. 3. As shown in FIG. 3, the specific activities are presented as a percent of the wildtype erythropoietin activity for each mutant erythropoietin. The amino acid replaced by alanine is indicated along the horizontal axis. Table I also shows the specific activities of the nine mutant erythropoietin proteins (SEQ ID NOS: 4–13) as well as nine additional mutant erythropoietin proteins (SEQ ID NOS: 14–22) again assayed in the first set of experiments. The specific activity noted in Table I is also that activity relative to wildtype erythropoietin's activity, which is set at 100%.

As shown in Table I, substitution of alanine for serine 104 decreased activity to approximately 16% of wildtype erythropoietin (SEQ ID NO: 14). Substitution of alanine for leucine 105 (SEQ ID NO: 9) reduced the activity to approximately 44 percent of wildtype erythropoietin. Substitution of alanine for leucine 108 (SEQ ID NO: 15) reduced the activity to approximately 37% of wildtype erythropoietin.

TABLE I

ALANINE SCANNING MUTAGENESIS OF AMINO ACIDS 100–109 OF ERYTHROPOIETIN

| MUTANT | OLIGONUCLEOTIDE | SPECIFIC ACTIVITY | SEQ ID NO: |
|---|---|---|---|
| S100A | GGATAAAGCCGTCGCTGGCCTTCGCAGCCTCACGACTCTGCTTCGGG | 107.9% | 4 |
| G101A | GCCGTCAGTGCCCTTCGCAGCCTCACGACTCTGCTTCGGG | 126.8% | 5 |
| L102A | GCCGTCAGTGGCGCTCGCAGCCTCACC | 93.3% | 6 |
| R103A | CGTCAGTGGCCTTGCCAGCCTCACGACTCTGCTTCGG | 0.0% | 7 |
| R103D | CGTCAGTGGCCTTGACAGCCTCACGACTCTGCTTCGG | 0.0% | 8 |
| L105A | GGCCTTCGCAGCGCCACGACTCTGCTTCGGG | 44.0% | 9 |
| T106A | GCCTTCGCAGCCTCGCGACTCTGCTTCGGGC | 76.9% | 10 |
| T107A | CGCAGCCTCACCGCTCTGCTTCGAGCTCTGCGAGCC | 86.6% | 11 |
| L108A/G113R | GCCTCACCACTGCCTTCGAGCTCTGCGAGCC | 77.3% | 12 |
| L109A/G113R | CCTCACCACTCTGGCTCGGGCTCTGCG | 84.7% | 13 |
| S104A | GTGGCCTTCGCGCCCTCACGACTCTGCTTC | 16.3% | 14 |
| L108A | CCTCACCACTGCGCTTCGAGCTCTGGGAGC | 36.9% | 15 |
| L109A | CCTCACCACTCTGGCTCGGGCTCTGGG | 70.2% | 16 |
| R103N | CGTCAGTGGCCTTAACAGCCTCACGACTCTGCTTCGG | 0.0% | 17 |
| R103E | CGTCAGTGGCCTTGAGAGCCTCACGACTCTGCTTCGG | 0.0% | 18 |
| R103Q | CGTCAGTGGCCTTCAGAGCCTCACGACTCTGCTTCGG | 0.0% | 19 |
| R103H | CGTCAGTGGCCTTCACAGCCTCACGACTCTGCTTCGG | 0.0% | 20 |
| R103L | CGTCAGTGGCCTTCTCAGCCTCACGACTCTGCTTCGG | 0.0% | 21 |
| R103K | CGTCAGTGGCCTGAAGAGCCTCACGACTCTGCTTCGG | 10.2% | 22 |

To further characterize the muteins obtained by substitution of the 103 arginine amino acid residue (SEQ ID NOS: 7, 8 and 17–22), a second set of experiments with COS-7 cells transfected as described in Example 2 with the pSV-2-erythropoietin mutant constructs encoding these muteins was performed. The supernatant medium was again harvested after three days and the biological activity of the mutant erythropoietin proteins was measured by the Krystal bioassay, the concentration of mutant erythropoietin protein was quantified by competitive radioimmunoassay (Incstar, Stillwater, Minn.) and specific activities (shown in Table II) were calculated as international units measured in the Krystal bioassay divided by micrograms as measured as immunoprecipitable protein by RIA.

TABLE II

MUTAGENESIS OF AMINO ACID Arg 103 OF ERYTHROPOIETIN

| MUTANT | OLIGONUCLEOTIDE | SPECIFIC ACTIVITY | SEQ ID NO: |
|---|---|---|---|
| R103A | CGTCAGTGGCCTTGCCAGCCTCACGACTCTGCTTCGG | 0.0% | 7 |
| R103D | CGTCAGTGGCCTTGACAGCCTCACGACTCTGCTTCGG | 0.0% | 8 |
| R103N | CGTCAGTGGCCTTAACAGCCTCACGACTCTGCTTCGG | 0.0% | 17 |
| R103E | CGTCAGTGGCCTTGAGAGCCTCACGACTCTGCTTCGG | 0.0% | 18 |
| R103Q | CGTCAGTGGCCTTCAGAGCCTCACGACTCTGCTTCGG | 0.0% | 19 |
| R103H | CGTCAGTGGCCTTCACAGCCTCACGACTCTGCTTCGG | 1.7% | 20 |

TABLE II-continued

MUTAGENESIS OF AMINO ACID
Arg 103 OF ERYTHROPOIETIN

| MUTANT | OLIGONUCLEOTIDE | SPECIFIC ACTIVITY | SEQ ID NO: |
|---|---|---|---|
| R103L | CGTCAGTGGCCTTCTCAGCCTCACGACTCTGCTTCGG | 0.4% | 21 |
| R103K | CGTCAGTGGCCTGAAGAGCCTCACGACTCTGCTTCGG | 25.0% | 22 |

As shown in Table II, mutants having arginine 103 substituted by histidine (SEQ ID NO: 20) exhibited decreased activity to approximately 1.7% of wildtype erythropoietin. Specific activity is again defined as percent activity of wildtype erythropoietin activity. Mutants having arginine 103 substituted by leucine (SEQ ID NO: 21) exhibited decreased activity to approximately 0.4% of wildtype erythropoietin. Mutants having arginine 103 substituted by lysine (SEQ ID NO: 22) exhibited decreased activity to approximately 25% of wildtype erythropoietin compared to approximately 10% of wildtype erythropoietin shown previously (compare Table I and Table II).

The results show that these three mutant erythropoietin proteins (SEQ ID NOS: 20–22) have some intrinsic agonist activity (biological activity), thus indicating that the erythropoietin muteins (SEQ ID NOS: 20–22) must bind to the erythropoietin receptor. This phenomenon of weak agonist activity is commonly seen in pharmacologic blockers when tested at high enough concentrations. Thus, it is reasonable to predict that equivalent quantities of these extremely low activity muteins would compete effectively with native erythropoietin and block activity.

As shown in Table II, mutants having arginine 103 substituted by alanine (SEQ ID NO: 7), aspartic acid (SEQ ID NO: 8), asparagine (SEQ ID NO: 17), glutamic acid (SEQ ID NO: 18), and glutamine (SEQ ID NO: 19) exhibited essentially no erythropoietin biological activity as was shown previously (Table I). The results of these experiments indicate that amino acid position 103 is important for erythropoietin biological activity. Although all of these mutants were expressed and secreted into culture medium at rates equivalent to that seen for wildtype and other mutants, only very low levels of biological activity were detected or, in some cases, no biological activity was detected. Methods described herein, such as the ex vivo bioassay of Krystal (Krystal, G., *Exp. Hematol.* 11:649–660 (1983)), which is an art-recognized bioassay used to evaluate erythropoietin activity, showed that these inactive arginine 103 mutants are reduced in activity by at least a 1000-fold below that of the wildtype human recombinant erythropoietin.

Previously published studies indicated that mutations in the Domain 1 region resulted in biologically inactive muteins. (Chern, Y., et al., *Eur. J. Biochem.* 202:225–229 (1991)). Thus, modified secretable erythropoietin proteins with mutations in the Domain 1 region would not be expected to have enhanced biological activity relative to wildtype erythropoietin proteins. That is, making mutations in this critical and highly conserved region of the erythropoietin protein would not be expected to result in the production of muteins with increased specific activity relative to wildtype erythropoietin proteins. Surprisingly, as shown in Table I, substitution of alanine for serine 100 (SEQ ID NO: 4) and glycine 101 (SEQ ID NO: 5) increased the specific activity of these mutant proteins.

To determine if the increased specific activity of the muteins obtained by substitution of alanine for serine 100 (S100A; SEQ ID NO: 4) and glycine 101 (G101A; SEQ ID NO: 5) was statistically significant, a statistical analysis based on the Student-t distribution for small samples was performed. The mean values obtained were compared to that of wildtype erythropoietin activity using the "difference between two sample means" statistic (one-sided). The increased specific activity of G101A over wildtype was found to be statistically significant at the 0.05 level of significance. The increased specific activity of S100A was not found to be statistically significant below the 0.010 level of significance.

Additionally, mutants having arginine 14 substituted by alanine (R14A) exhibited decreased activity to approximately 16.4% of wildtype erythropoietin. Mutants having arginine 14 substituted by aspartic acid (R14D) exhibited decreased activity to approximately 3.9% of wildtype erythropoietin.

STRUCTURAL INTEGRITY OF MUTANT ERYTHROPOIETIN PROTEINS

Previously published studies indicated that mutations in the Domain 1 region in which a group of three amino acids was deleted and replaced with Glu-Phe, caused pronounced structural changes in the molecule. (Chern, Y., et al., *Eur. J. Biochem.* 202:225–229 (1991)). These structural changes were accompanied by lack of secretion of the mutant erythropoietin from the transfected COS-7 cells. Surprisingly, this phenomenon was not observed with the more subtle mutations of the present invention. Thus, the mutant erythropoietin proteins described herein provide structurally intact (i.e., with the proper biological conformation) mutant erythropoietin proteins.

Assessment of the structural integrity of the mutated erythropoietin proteins of the instant invention was performed by a series of immunoprecipitation experiments using anti-peptide monoclonal antibodies to two domains of the protein, as described in Example 3.

Briefly, the first monoclonal antibody recognizes an epitope within amino acids 1–26 of erythropoietin. The other monoclonal antibodies recognize distinct epitopes within amino acids 99–129. It is known that a gross change in the tertiary structure of erythropoietin would result in an inability of one or more of the monoclonal antibodies to recognize the erythropoietin molecule. For example, it has been demonstrated that radio-iodination of erythropoietin in the presence of chloramine-T denatures the molecule, resulting in loss of biological activity and corresponding loss of recognition by monoclonal antibody.

Figure 4:
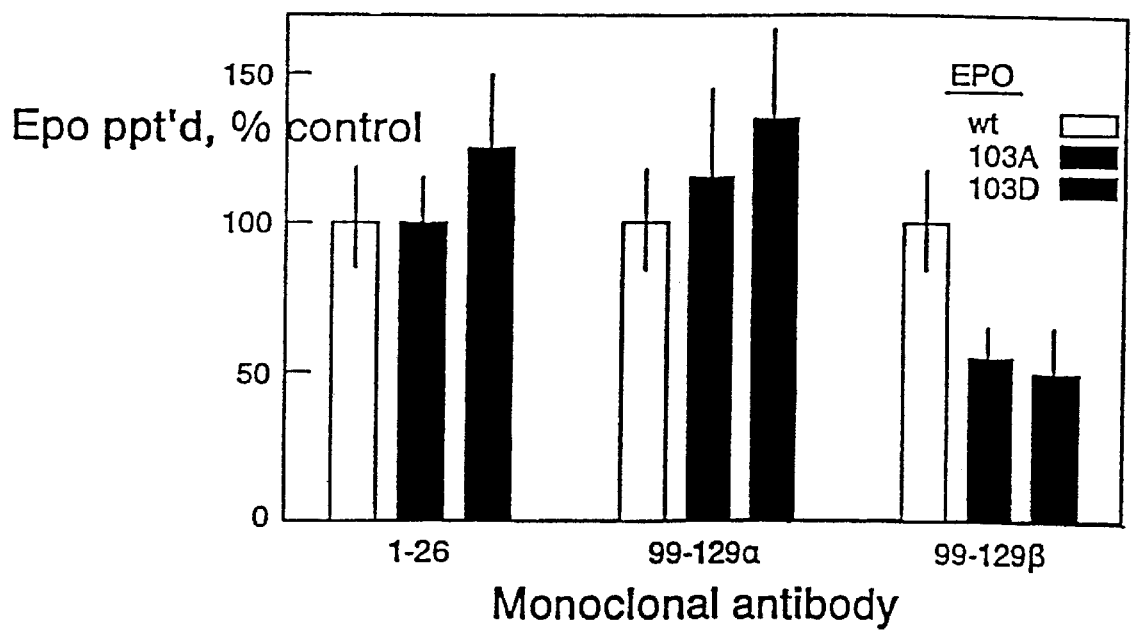
FIG. 4 is a graphic representation of the results of monoclonal antibody precipitation of the mutant erythropoietin proteins.

FIG. 4 shows mutant erythropoietin protein precipitated as percent of control of wildtype erythropoietin precipitated using three monoclonal antibodies designated across the horizontal axis, 1–26, 99–129α and 99–129β. The three erythropoietin proteins examined were the wildtype erythropoietin, the 103 alanine mutant and the 103 aspartic acid mutant. As seen on the left side of the graph, monoclonal 1–26 recognized each of the three recombinant erythropoietin proteins with equal efficiency, indicating that mutation of amino acid 103 to either alanine or aspartic acid did not result in a gross distortion of erythropoietin's conformation.

Similarly, as shown in the center of the graph, monoclonal 99–129α also recognized the wildtype 103 alanine mutant and 103 aspartic acid mutant with no statistically significant difference among them. This indicates that the conformation within the amino acids 99–129 is similar among the three recombinant erythropoietin proteins.

Lastly, as shown on the right side of the graph, monoclonal 99–129β recognized both mutant erythropoietin proteins with approximately half the efficiency as it recognized the wildtype erythropoietin. This is consistent with the subtle structural change introduced by a single amino acid mutation. Taken together, it is reasonable to assume that the inactive point mutants, 103 alanine and 103 aspartic acid, are not grossly denatured.

HEAT STABILITY OF MUTANT ERYTHROPOIETIN PROTEINS

A previously published study indicated that recombinant human erythropoietin aggregates as temperature rises. (Endo, Y., et al., *J. Biochem.* 112(5):700–706 (1992)). Most of the erythropoietin molecules within these multimeric aggregates (twenty erythropoietin molecules per aggregate) would almost certainly not be detectable by antibodies in a radioimmunoassay (RIA). Surprisingly, heat reduced the RIA detection of wildtype erythropoietin much more rapidly than the more stable mutants of the present invention. Thus, some of the mutant erythropoietin proteins described herein demonstrate increased heat stability relative to the wildtype erythropoietin protein.

Assessment of the heat stability of the mutated erythropoietin proteins of the instant invention was performed by comparing in vitro biological activity with antibody reactivity. Briefly, aliquots of conditioned medium from erythropoietin cDNA-transfected COS cells were incubated at 56° C. for specified time intervals. The samples were cooled on ice and a fraction of each was assessed for biological activity in the Krystal bioassay. The remainder was split into two fractions and erythropoietin protein was quantified by radioimmunoassay using the commercially available INCSTAR RIA kit. The results are given in terms of the percent biological activity remaining or percent protein immunoprecipitated after heat treatment compared to untreated samples.

Figure 5:
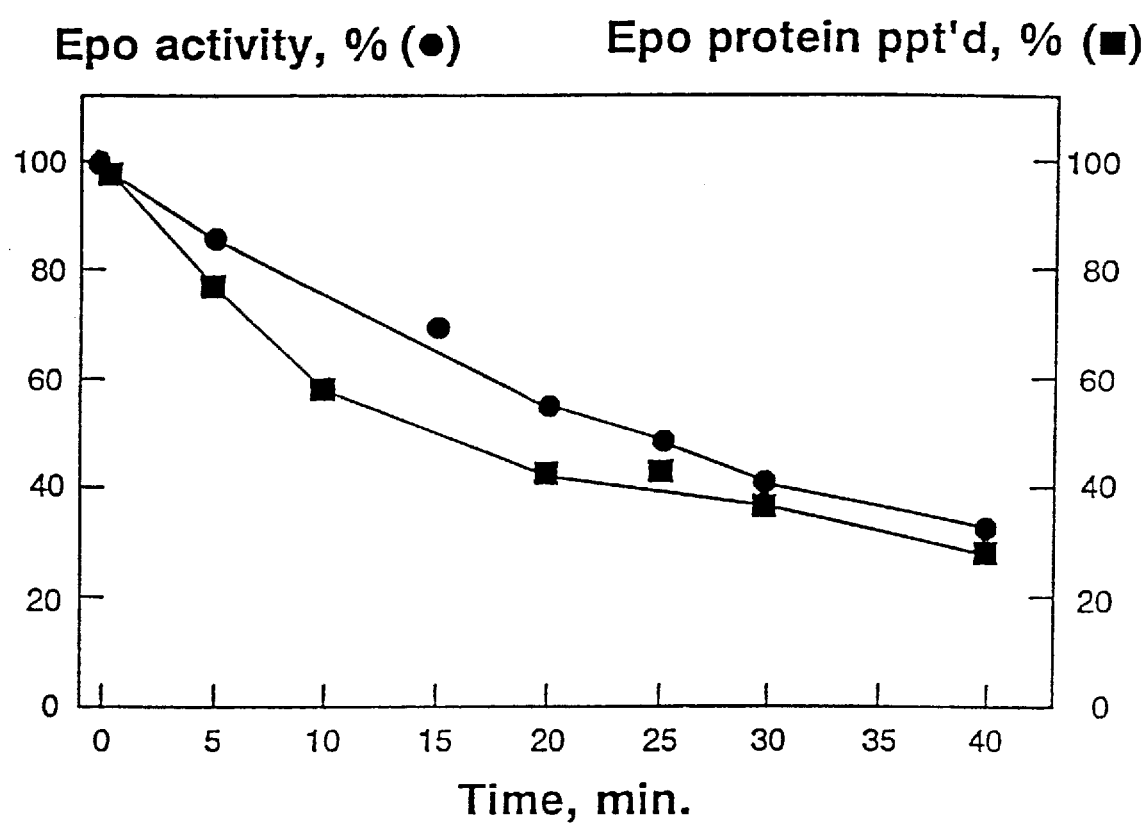
FIG. 5 is a graphic representation of the activity of heat-denatured wildtype erythropoietin as measured by radioimmunoassay (■) and the Krystal bioassay (●).
Figure 6A:
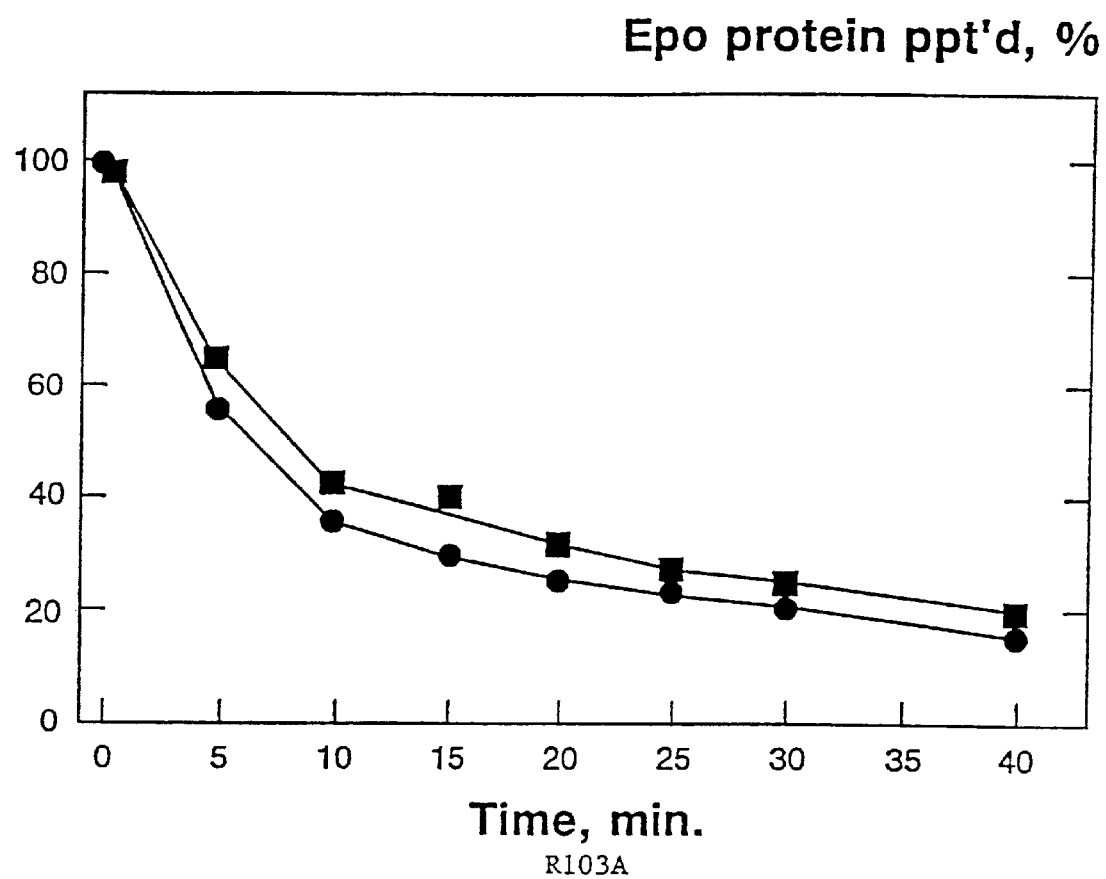
FIGS. 6A–6H is a graphic representation of the activity of the 103 mutant erythropoietin proteins as measured by radioimmunoassay (■) and the activity of wildtype erythropoietin (●).

Wildtype erythropoietin exhibits a time-dependent decrease in biological activity when incubated at 56° C. or above (FIG. 5); Tsuda, E., et al., *Eur. J. Biochem.* 188:405–411 (1990). Interestingly, a corresponding decrease in the ability of the commercial radioimmunoassay's antibodies to recognize this heat-denatured erythropoietin was also observed (FIG. 5). This observation was quite reproducible and enabled the use of the RIA to measure the heat stability of the inactive R103A erythropoietin compared to that of wildtype erythropoietin. As seen in FIG. 6A, the heat denaturation curves of R103A and wildtype erythropoietin are essentially identical.

Figure 6B:
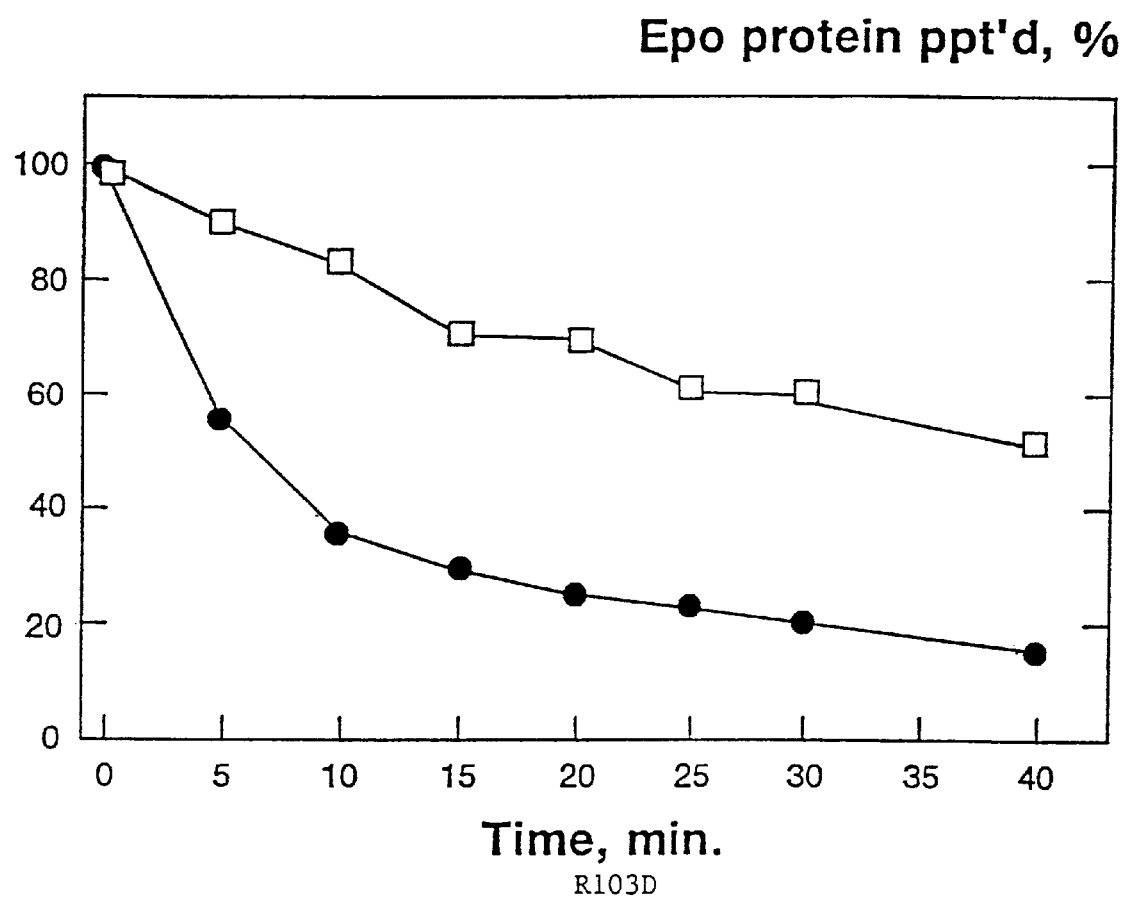
Figure 6C:
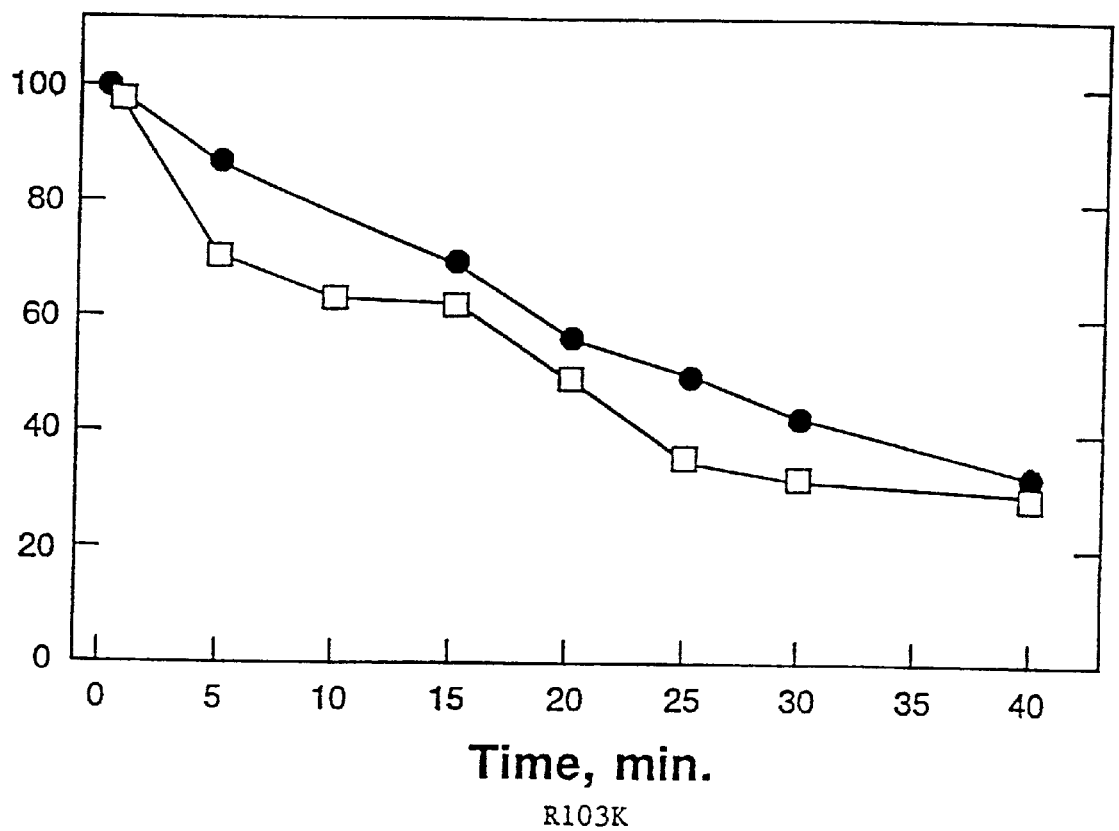
Figure 6D:
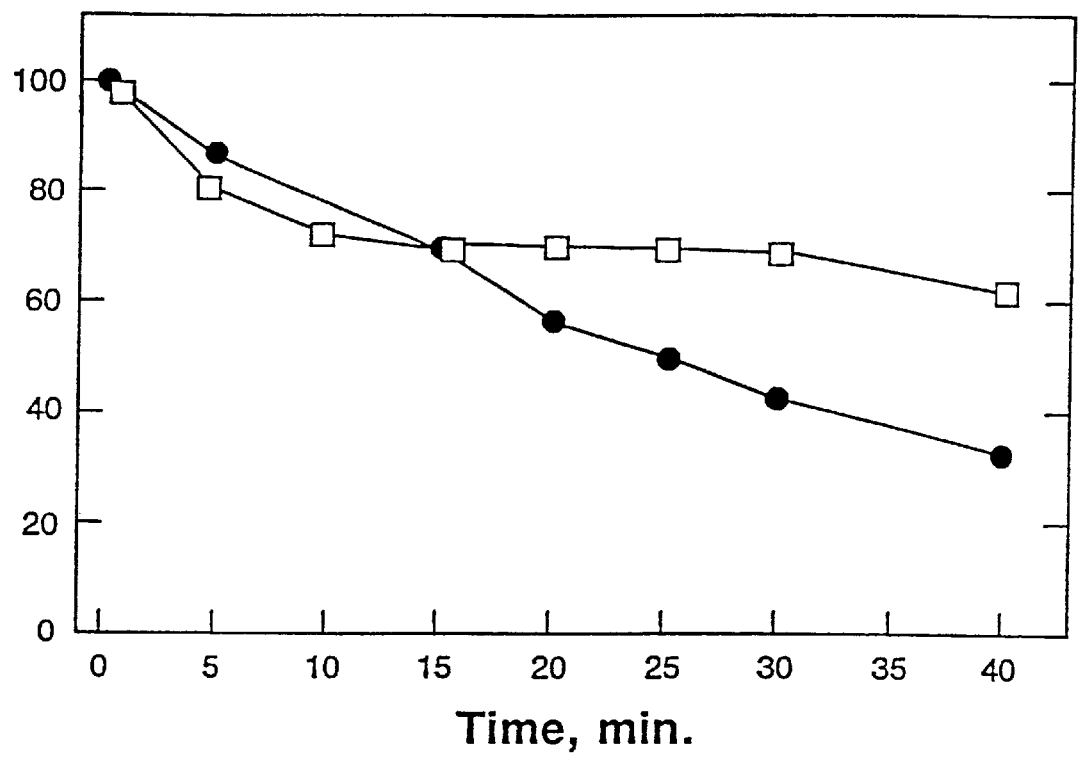
Figure 6E:
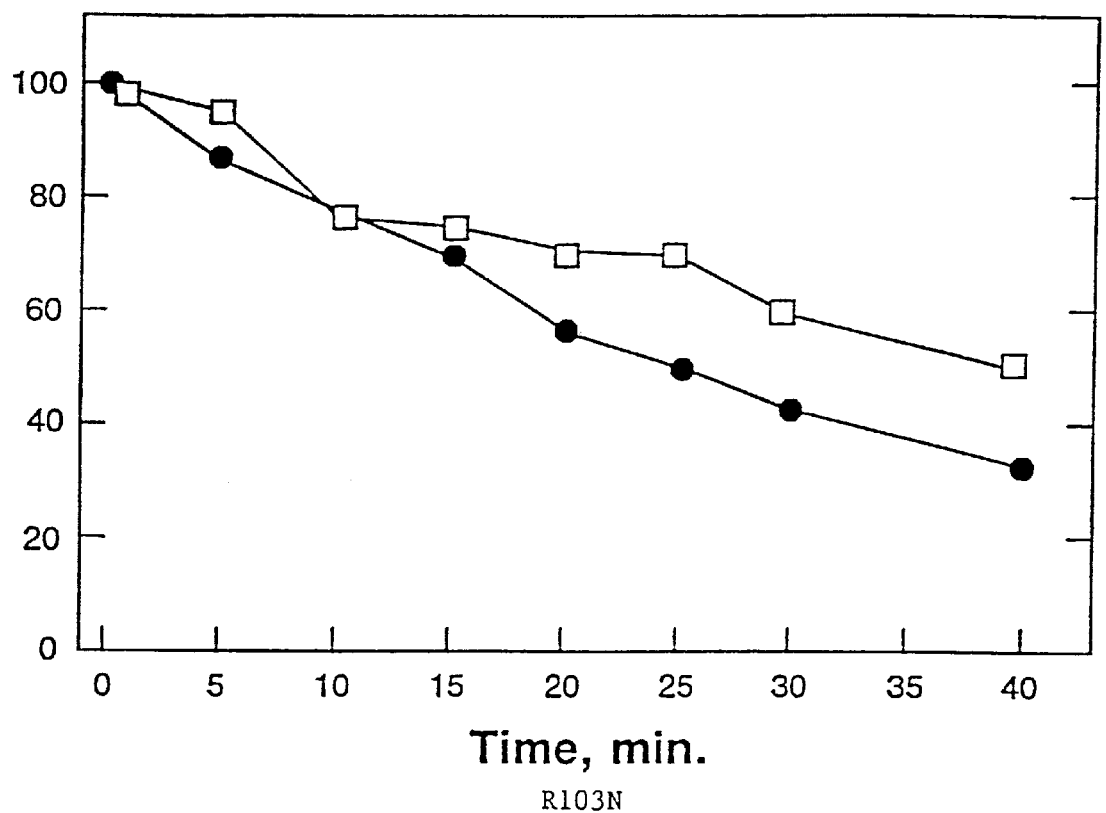
Figure 6F:
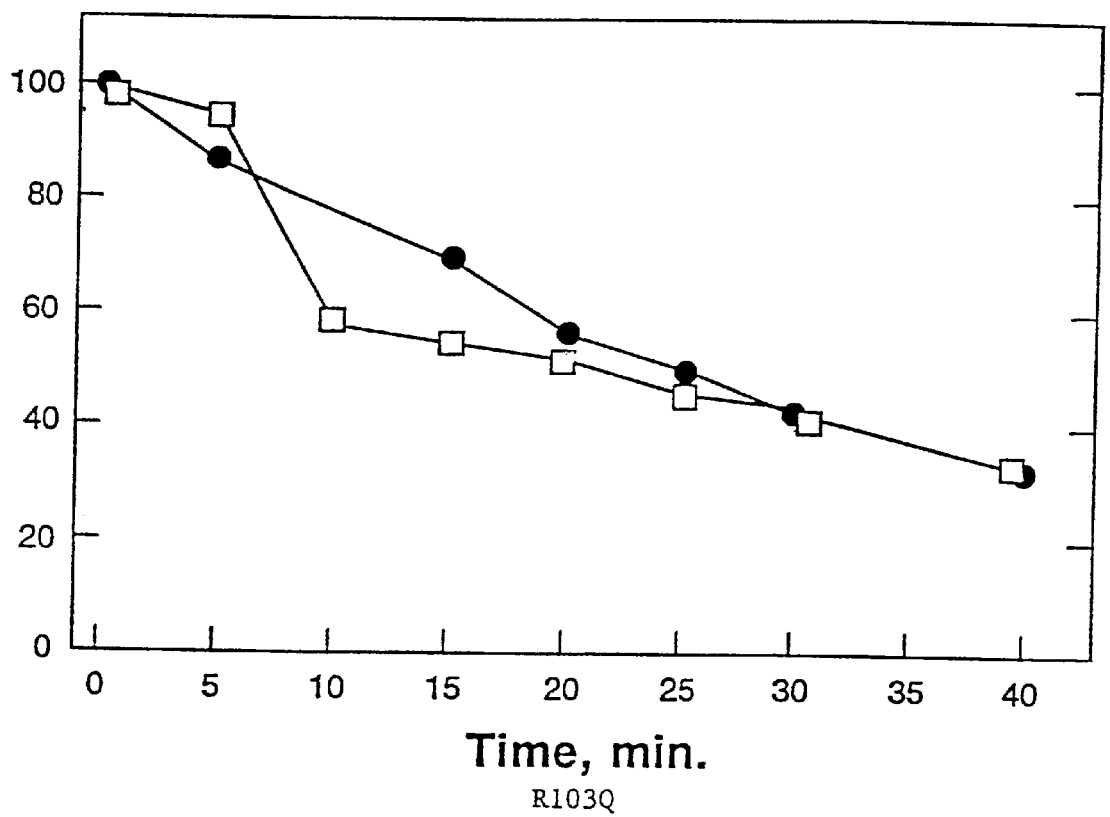
Figure 6G:
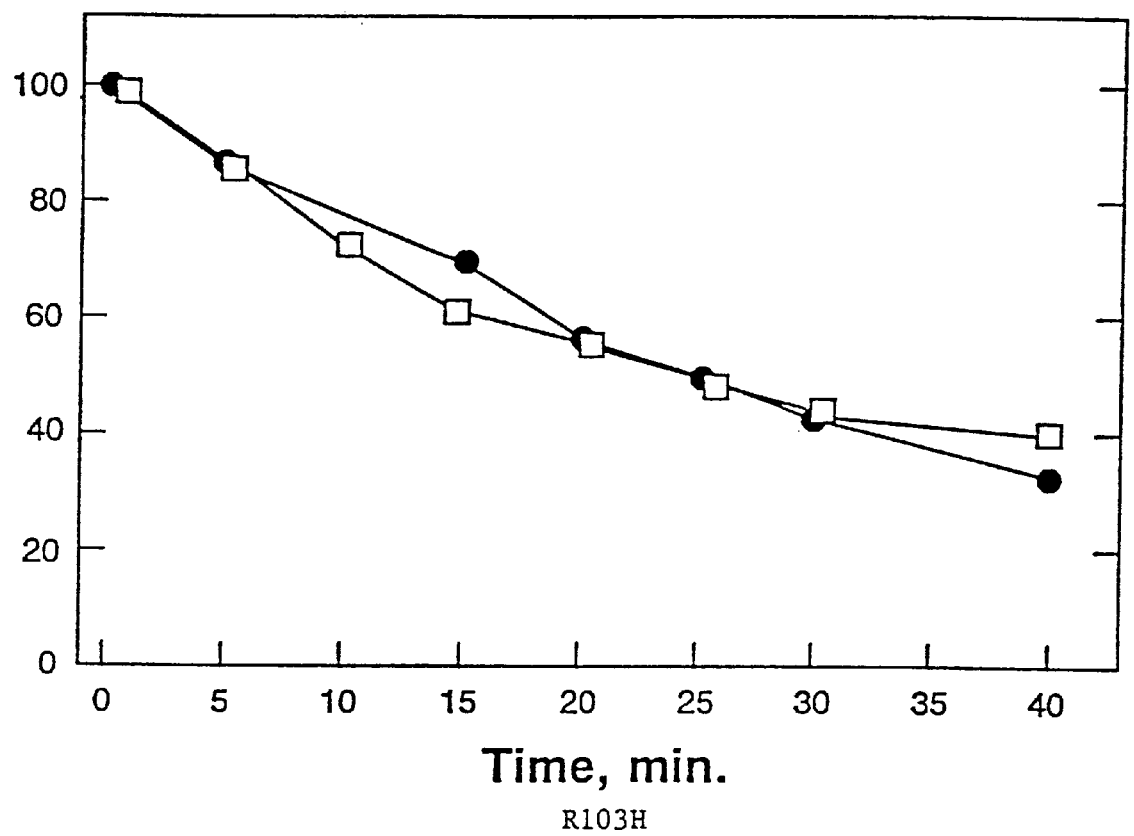
Figure 6H:
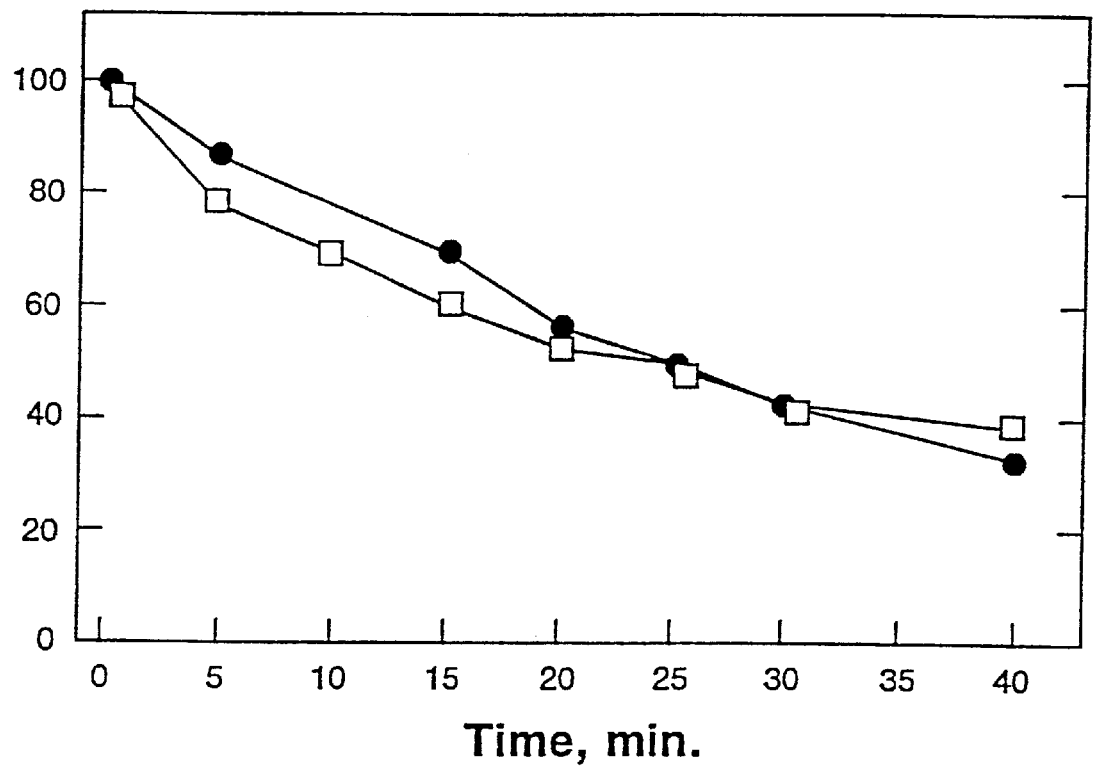

To confirm that this heat stability comparison is sensitive to mutations in this region of erythropoietin, the effect of the aspartic acid substitution (R103D) on the protein's stability was evaluated. The introduction of a negatively charged amino acid residue would reasonably be more structurally disruptive to the molecule than an alanine, and thus be more likely to alter the protein's heat-denaturation curve. The heat stability of R103D was markedly different (i.e., greater) than that of wildtype erythropoietin and R103A, as anticipated (FIG. 6B).

To further characterize the nature of the interaction between amino acid residue 103 and the erythropoietin receptor, site-directed mutagenesis was used to produce erythropoietin analogs with altered side chain properties at this position. Arginine was substituted with histidine (R103H), lysine (R103K), asparagine (R103N), glutamine (R103Q), leucine (R103L) and glutamic acid (R103E) to generate 6 new altered erythropoietin molecules. Culture supernatants of cells transfected with these constructs in a first set of experiments were tested in the Krystal bioassay and the heat stability assay for biological activity and structural stability, respectively.

The heat denaturation curve of R103K was essentially identical to that generated for the wildtype protein. Interestingly, the heat denaturation curve for R103E was notably different from that of wildtype, and very similar to that of R103D. The other 4 mutants had denaturation kinetics intermediate to that of these two proteins. (See FIGS. 6C–6H).

PRODUCTION OF ADDITIONAL ERYTHROPOIETIN PROTEINS HAVING ALTERED BIOLOGICAL ACTIVITY

As a result of the identification of sites which are critical to erythropoietin activity in terms of the amino acid residue present and which can be altered to produce a mutated sequence which has altered biological activity but retains its structural integrity, it is now possible to produce modified secretable human recombinant erythropoietin proteins whose ability to regulate the growth and differentiation of red blood cell progenitors is altered (i.e., whose ability to regulate red blood cell progenitors is different from that of the corresponding wildtype human recombinant erythropoietin). These modified human recombinant erythropoietin proteins can be secreted in homologous or heterologous expression systems.

As described in the previous sections and in the Examples, such sites have been identified by oligonucleotide-directed mutagenesis and used to create mutant erythropoietin which resulted in substitution of amino acids at positions 100–109 within Domain 1 (SEQ ID NO: 1), as represented in FIG. 1 (SEQ ID NOS: 4–13) and Table I (SEQ ID NOS: 4–16). The data indicate that arginine 103 is critical for erythropoietin's biological activity. Additionally, serine 104, leucine 105 and leucine 108 appear to play a role, as indicated by the decreased biological activity of these mutants as measured in the above-described bioassays.

It is important to note that the ability of erythropoietin to regulate growth and differentiation of red blood cell progenitors depends on the ability of erythropoietin to bind to its cellular receptor. Importantly, the mutations described herein do not disrupt the structural integrity of the erythropoietin protein, as evidenced by the fact that the mutated protein is secreted. That is, as the data presented herein indicates, these mutant erythropoietin proteins retain their biological conformation. These results also indicate that Domain 1 amino acids 99–110 very likely participate in receptor recognition and activation.

Moreover, as the data presented herein indicates, some mutant erythropoietin proteins also demonstrate increased heat stability relative to the wildtype erythropoietin, even though the biological activity of the mutant has been significantly decreased.

Substitution of alanine at arginine 103 produced erythropoietin mutants with no detectable erythropoietin activity as measured by standard techniques. Mutations at serine 104, leucine 105 and leucine 108 also significantly decreased biological activity relative to wildtype erythropoietin activity. In a similar manner, other changes at one or more of these critical sites can result in reduction of erythropoietin activity. Conversely, amino acid residues can be introduced at these critical sites to produce modified secretable human recombinant erythropoietin proteins with enhanced biological activity relative to wildtype erythropoietin activity.

Conservative substitutions can be made at one or more of the amino acid sites within residues 100–109 of the molecule. For example, alanine and aspartic acid have been used to replace arginine 103. Substitution of these amino acids by other amino acids of the same type (i.e., a positively charged, or basic, amino acid for a positively charged, or basic, one, or an acidic amino acid for an acidic one) as that present at that specific position can be made and the effect on erythropoietin's ability to regulate the growth and differentiation of red blood cell progenitors can be determined, using the methods described herein.

Substitutions at these critical sites, alone or in combination, of amino acids having characteristics different from those of amino acids whose presence at those sites has been shown to eliminate or reduce erythropoietin activity can also be made and their effect on activity assessed as described above. In particular, substitutions of some, or all, of the amino acids at one, or more, of these critical sites which result in modified secretable erythropoietin proteins with enhanced erythropoietin activity can be made. Using the techniques described herein, erythropoietin proteins having enhanced biological activity can be identified.

In addition, more radical substitutions can be made. For example, an amino acid unlike the residue present in the corresponding position in the wildtype sequence is substituted for the residue in wildtype erythropoietin (e.g., a basic amino acid is substituted for an acidic amino acid). Each resulting mutant is then evaluated using the anti-erythropoietin immunoprecipitation techniques and biological activity assays as described.

As a result, modified secretable human recombinant erythropoietin proteins having enhanced erythropoietin activity or increased heat stability can be identified. Similar techniques can be used to identify additional critical sites and subsequently, to make substitutions and evaluate their effects on erythropoietin regulating activity.

The present invention also relates to modified erythropoietin variant mutant proteins encoded by nucleic acids that contain alterations in noncoding regions of the gene in addition to mutations in coding regions as described above.

The variant nucleic acid molecules encoding, for example, modified erythropoietin variant mutant proteins created by altering the 3' and/or 5' UTR of the erythropoietin gene, would preferably contain regulatory sequences. Regulatory sequences include all cis-acting elements that control transcription and regulation such as, promoter sequences, enhancers, ribosomal binding sites, and transcription binding sites. Selection of the promoter will generally depend upon the desired route for expressing the protein. For example, where the mutein erthropoietin variant protein is to be expressed in a recombinant eukaryotic or prokaryotic cell, the selected promoter is recognized by the host cell. A suitable promoter which can be used can include the native promoter for the binding moiety which appears first in the construct.

The elements which comprise the nucleic acid molecule can be isolated from nature, modified from native sequences or manufactured de novo, as described, for example, in the several art-recognized laboratory technical protocol texts such as Sambrook, et al., "Molecular Cloning: A Laboratory Manual," (1989) and Ausubel, et al. "Current Protocols in Molecular Biology," (1995). The elements can then be isolated and fused together by methods known in the art, such as exploiting and manufacturing compatible cloning or restriction sites.

The nucleic acid molecules encoding modified erythropoietin variant proteins can be inserted into a construct which can, optionally, replicate and/or integrate into a recombinant host cell, by known methods which may vary depending upon the form of the recombinant erythropoietin mutein which is expressed. The host cell can be a eukaryotic or prokaryotic cell and includes, for example, pichia expression systems, yeast (such as, Saccharomyces), bacteria (such as, Escherichia or Bacillus), animal cells or tissue, including insect (such as, Spodoptera frugiperda 9) or mammalian cells (such as, somatic or embryonic human cells, Chinese hamster ovary cells, HeLa cells, human 293 cells, monkey kidney COS-7 cells, baby hamster kidney BHK cells, C127 cells, etc.). The selection of the host cell governs the posttranslational modifications that may occur. For instance, glycoproteins could be expressed in mammalian, insect, or yeast cells whereas nonglycosylated protein could be expressed in bacteria.

In addition, the selection of the appropriate host cell may differ when expressing recombinant modified erythropoietin variant proteins manufactured by alterations in the noncoding regions of the gene. (Schultz, et al., J. Virol. 70:1041–1049, 1996).

The nucleic acid molecule can be incorporated or inserted into the host cell by known methods. Examples of suitable methods of transfecting or transforming cells include calcium phosphate precipitation, electroporation, microinjection, infection, lipofection and direct uptake. Methods for preparing such recombinant host cells are described in more detail in several technical books, for example, Sambrook, et al., (supra) and Ausubel, et al. (supra).

The host cells are maintained under suitable conditions for expressing and recovering the recombinant modified erythropoietin variant protein. Generally, the cells are maintained in a suitable buffer and/or growth medium or nutrient source for growth of the cells and expression of the gene product(s). The growth media are generally known in the art and include sources of carbon, nitrogen and sulfur. Examples include Dulbeccos modified Eagles media (DMEM), RPMI-1640, M199 and Grace's insect media. The selection of a buffer is not critical to the invention. The pH which can be selected is generally one tolerated by or optimal for growth for the host cell.

The cell is maintained under a suitable temperature and atmosphere. For example, an aerobic host cell is maintained under aerobic atmospheric conditions or other suitable conditions for growth. The temperature should also be selected so that the host cell tolerates the process and can be, for example, between about 27° C. and 40° C.

APPLICATIONS OF MODIFIED SECRETABLE ERYTHROPOIETIN PROTEINS HAVING ALTERED BIOLOGICAL ACTIVITY

As described above, arginine 103 is essential for erythropoietin's biological activity. Additionally, serine 104, leucine 105 and leucine 108 also appear to play a significant role in biological activity. Furthermore, these subtle point mutations do not compromise the structural integrity, (i.e., secretability) of the erythropoietin molecule. Since these described muteins have some intrinsic biological activity as detected by the assays described herein, albeit significantly reduced from wildtype erythropoietin, it is reasonable to assume that they do bind to the erythropoietin receptor. Thus, it is reasonable to assume that the mutant erythropoietin proteins will be recognized by the erythropoietin cellular receptor in essentially the same manner as the wildtype erythropoietin.

Modified secretable human recombinant erythropoietin proteins of the present invention can be used for therapy and diagnosis of various hematologic conditions. For example, an effective amount of modified secretable recombinant erythropoietin with enhanced biological activity to regulate the growth and differentiation of red blood cell progenitors can be used therapeutically (in vivo) to treat individuals who are anemic (e.g. as a result of renal disease, chemotherapy, radiation therapy, or AIDS). An effective amount of modified secretable human recombinant erythropoietin protein, as defined herein, is that amount of modified secretable erythropoietin protein sufficient to regulate growth and differentiation of red blood cell progenitor cells. For example, modified secretable erythropoietin protein with increased regulatory ability will bind to the erythropoietin receptor and stimulate the growth and differentiation of red blood cell progenitor cells. The modified secretable erythropoietin with enhanced biological activity would be more potent than the wildtype erythropoietin. Thus, to increase red blood cell growth and differentiation in anemic conditions, a lower effective dose or less frequent administration to the individual would be required.

Modified secretable erythropoietin with altered regulating activity can also be used to selectively trigger only certain events regarding the growth and differentiation of red blood cell precursors. For example, it has recently been shown that binding of erythropoietin to its receptor generates two distinct chemical signals in cells, a protein kinase C dependent activation of the proto-oncogene c-myc and a phosphatase mediated signal to c-myb. (Spangler, R., et al., *J. Biol. Chem.* 266:681–684 (1991); Patel, H. R. and Sytkowski, A. J., Abstract 1208, *Blood* 78(10) Suppl. 1 (1991)). Thus, a modified secretable erythropoietin can be used to selectively activate either the protein kinase C or the phosphatase pathways.

An effective amount of modified secretable erythropoietin with decreased biological activity relative to wildtype erythropoietin activity, (i.e., reduced biological activity or no detectable biological activity), can be used to treat individuals with various erythroleukemias. In this case, an effective amount of modified secretable erythropoietin protein with decreased regulatory ability will bind to the erythropoietin cellular receptor. However, upon the mutant erythropoietin protein binding to the receptor, it is reasonable to predict that the mutant protein lacks ability to trigger subsequent erythropoietin events. It is further reasonable to predict that, because the mutant erythropoietin does bind to the receptor, it prevents wildtype erythropoietin from binding to the receptor (i.e., competitively inhibits the binding of wildtype erythropoietin). Thus, the red blood cell progenitors do not proliferate and/or differentiate.

The mutant erythropoietin proteins of the present invention are secretable, indicating that they retain their structural integrity, and thus fully participate in receptor recognition and binding. The initial interaction of a hormone with its cognate receptor might be expected to result in further conformational changes of the hormone ligand, thereby stabilizing the hormone/receptor complex and allowing the formation of higher ordered complexes. However, if a modified erythropoietin protein of the present invention, with no detectable erythropoietin activity, binds to its receptor, it is reasonable to assume that the subsequent events triggered by receptor binding will be altered or inhibited. Therefore, it is also reasonable to assume that growth and differentiation of red blood cell progenitor cells will be altered or inhibited, thereby inducing a remission in a red blood cell leukemia.

Recently, a constitutively active (hormone independent) form of the murine erythropoietin receptor was isolated. (watowich, S. S., *Proc. Natl. Acad. Sci. USA* 89:2140–2144 (1992)). It has also been shown that the envelope glycoproteins of certain murine viruses bind to and activate the murine erythropoietin receptor. (Yoshimura, A., *Proc. Natl. Acad. Sci. USA* 87:4139–4143 (1990)). Thus, erythropoietin-independent activation (constitutive activation) of the erythropoietin receptor resulting in red blood cell proliferation in a mammal has been demonstrated. It is reasonable to predict that similar constitutive activation would occur in humans, (for example, a virus similar to Rauscher or Friend virus) may constitutively activate the human erythropoietin receptor also resulting in proliferation of red blood cell progenitors. A modified secretable erythropoietin, which retains its structural integrity to bind to the receptor, yet does not activate red blood cell proliferation, would be useful as an antagonist to block such constitutive activation. Moreover, modified secretable erythropoietin proteins with increased stability would provide longacting erythropoietin antagonists.

Modified secretable erythropoietin would be useful to treat other various medical disorders. For example, polycythemia vera is characterized by uncontrollable proliferation of red blood cells and is currently treated by chemotherapy, radiation or phlebotomy. The increased number of red blood cells increases blood viscosity, leading to a hypertensive condition that can result in a stroke. It is reasonable to predict that an antagonist of erythropoietin, which binds to the receptor and blocks activation, would be a useful, non-invasive treatment.

Likewise, individuals with cyanotic heart disease often have a hyper-erythropoietin condition, leading to increased erythrocyte proliferation. Also, renal disease patients that are being treated with wildtype erythropoietin may experience an overdose. Once the wildtype erythropoietin has been administered, it continues to act. Thus, in these cases, it would be useful to administer a modified secretable erythropoietin with decreased activity to block the effects of the endogenous and exogenous erythropoietin.

Furthermore, certain hemolytic anemias, such as sickle cell anemia and thalassemia, result in rapid destruction of red blood cells. The body responds by increasing the levels of erythropoietin produced to stimulate red blood cell production. However, the red blood cells produced carry defective hemoglobin. It would be useful to use a modified secretable erythropoietin to reduce production of defective erythrocytes while another form of therapy is used to stimulate normal hemoglobin synthesis.

Erythropoietin has a relatively short plasma half-life (Spivak, J. L. and Hogans, B. B., *Blood* 73: 90–99 (1989); McMahon, F. G., et al., *Blood* 76: 1718–1722 (1990)), therefore, therapeutic plasma levels are rapidly lost, and repeated intravenous administrations must be made.

Although the mechanisms responsible for this relatively short plasma half-life are not well understood, inactivation due to heat denaturation/aggregation is likely to play a role. A previously published study indicated that erythropoietin in human serum is susceptible to inactivation by heat. (Elder, G. E., et al., *Blood Cells* 11: 409–419 (1986)). Thus, it is reasonable to predict that modified secretable erythropoietin with increased heat stability relative to wildtype erythropoietin would have a longer plasma half-life relative to wildtype erythropoietin and thus, be useful therapeutically. This may be especially important in patients with a fever and/or an increased metabolic state.

It is also reasonable to predict that modified secretable erythropoietins with enhanced biological activity relative to wildtype erythropoietin would require a smaller quantity relative to wildtype erythropoietin to achieve a specified level of biological activity. This enhanced biological activity indicates that an effective amount of modified erythropoietin with enhanced biological activity is substantially less than a comparable effective amount of wildtype erythropoietin. The effective amount of modified erythropoietin with enhanced biological activity is defined herein as the amount of modified erythropoietin required to elicit an erythropoietin response, as indicated by increased growth and/or differentiation of erythrocytic precursor cells. Further, the effective amount of modified erythropoietin with enhanced biological activity will require less frequent administration than an equivalent amount of wildtype erythropoietin. For example, if an effective dose of erythropoietin is typically administered three times a week, modified erythropoietin with enhanced biological activity will only need to be administered once a week. Thus, a reduced quantity of modified secretable erythropoietin with enhanced biological activity would be necessary over the course of treatment than would be necessary if wildtype erythropoietin were used.

Modified secretable erythropoietin may be administered to individuals parenterally or orally. The modified secretable erythropoietin proteins of this invention can be employed in admixture with conventional pharmaceutically acceptable carriers. Suitable pharmaceutical carriers include, but are not limited to, water, salt solutions and other physiologically compatible solutions. The modified secretable erythropoietin proteins of the present invention may be administered alone, or combined with other therapeutic agents.

It will be appreciated that the amount of modified secretable erythropoietin administered to an individual in a specific case will vary according to the specific modified secretable erythropoietin protein being utilized, the particular compositions formulated, and the mode of application. Dosages for a given individual can be determined using conventional considerations such as the severity of the condition, body weight, age and overall health of the individual.

Modified secretable erythropoietin can also be used for diagnostic purposes. For example, it can be used in assay procedures for detecting the presence and determining the quantity, if desired, of erythropoietin receptor. A modified secretable erythropoietin with enhanced activity would be useful to increase the sensitivity and decrease the incubation times of such assays. It can also be used in in vitro binding assays to determine the effect of new drugs on the binding of erythropoietin protein to its receptor.

Modified secretable erythropoietin proteins described herein also provide useful research reagents to further elucidate the role of erythropoietin in erythropoiesis, as well as the structure/function relationship of erythropoietin and its cellular receptor. For example, modified secretable erythropoietin proteins may be useful for evaluating a substance for ability to regulate growth and differentiation of red blood cell progenitor cells. A reasonable indication of the ability of a substance to regulate growth and differentiation of red blood cell progenitor cells is the extent of binding of the substance to the erythropoietin receptor. The term, extent of binding, as used herein, is defined to mean the amount of substance bound to the receptor (e.g., the percent of substance bound to the receptor as compared to a control substance that binds at approximately 100 percent, or alternately, the specific activity of the test substance). A method for evaluating a substance for ability to regulate growth and differentiation of red blood cell progenitor cells can comprise comparing the extent of binding to the erythropoietin receptor of the substance to be evaluated with the extent of binding to the erythropoietin receptor of a modified secretable mutant erythropoietin protein. If the extent of binding to the erythropoietin receptor of the test substance (i.e., the substance to be evaluated) is comparable to the extent of binding to the erythropoietin receptor of the modified secretable mutant erythropoietin protein, then the extent of binding of the test substance is an indication that the ability of the substance to regulate growth and differentiation of red blood cell progenitor cells is of approximately the same ability as the modified secretable mutant erythropoietin. For example, if the specific activity of a test peptide is 25.0%, it is reasonable to assume that the test peptide has the ability to regulate growth and differentiation of red blood cell progenitor cell comparable to the R103K modified erythropoietin.

The term substance, as used herein, is defined to include proteins, e.g., analogues of wildtype erythropoietin, erythropoietin protein fragments, other proteins or peptides, and drugs.

The extent of binding to the erythropoietin receptor can be determined by using any of a number of methods familiar to those of skill in the art. For example, methods such as those described in Yonekura, S. et al., *Proc. Natl. Acad. Sci. USA* 88:1–5 (1991); Chern, Y. et al., *Blood* 76(11):2204–2209 (1990); and Krystal, G., *Exp. Hematol.* 11:649–660 (1983), the teachings of which are incorporated herein by reference, may be used.

The modified erythropoietin mutant proteins of the invention produced, for example, by altering the 5' and/or 3' UTR, can be used as therapeutics for delivery to individuals having diseases or conditions that are associated with deficiencies or abnormalties of the proteins described herein. The retention and/or deletion of nucleotides in the UTR of the erythropoietin gene can produce heterologous therapeutic proteins. Heterologous proteins are herein defined as proteins which do not exist in nature and exhibit a range of therapeutic effects.

Recombinant erythropoietin proteins with therapeutic value are known in the art. Examples include Lin (U.S. Pat. No. 4,703,008); Sytkowski and Grodberg (U.S. Pat. No. 5,614,184); Sytkowski (U.S. Pat. No. 5,580,853); and Powell (U.S. Pat. No. 5,688,679): the contents of which are incorporated herein by reference.

For example, the modified erythropoietin proteins described herein can be employed in any method where EPO would be effective, and in particular in methods where other man-made erythropoietin proteins have not produced any clinically beneficial effect (e.g., increasing red blood cells in an anemic patient). The mode of erythropoietin administration to patients is preferably at the location of the target cells. As such, the administration can be by injection. Other modes of administration (parenteral, mucosal, systemic, implant, intraperitoneal, etc.) are generally known in the art and, for erythropoietin, can be determined, for example, as described in U.S. Pat. No. 5,614,184. The recombinant erythropoietin proteins can, preferably, be administered in a pharmaceutically acceptable carrier, such as saline, sterile water, Ringer's solution, and isotonic sodium chloride solution.

The activity of modified erythropoietin proteins, including variants produced by alterations in the 5' and/or 3' UTR, can be tested, for example, in pharmacological differences. Accordingly, the activity of modified erythropoietin proteins can be evaluated therapeutically. For example, pharmacological differences in the secreted and purified erythropoietin manufactured by the disclosed method compared to other man-made or naturally occurring erythropoietins can include:

1. An increase or decrease in the potency when administered to patients in human clinical trials. The difference can be in the required initial dose as well as maintenance doses. A relative potency factor can be evaluated for the modified erythropoietin proteins.
2. A reduction or increase in potential side effects in patients may reflect altered activities of the modified erythropoietin proteins. For example, differences can be manifested as an increase or decrease in blood pressure which can be of extraordinary significance in designing treatment regimens for certain high risk patients like dialysis patients who are, in any case, severely ill.
3. A difference in the time lag between the effect of increasing red blood cells in the patient's serum after administration of the modified erythropoietin proteins. This time-lag has the consequence that the desired therapeutic effect is either accelerated or delayed significantly compared to other forms of erythropoietin. A decrease in the time lag would be a desirable therapeutic effect by resulting in a faster benefit to the patient.
4. The ability of a patient to tolerate one form of erythropoietin and not another. If a patient can not tolerate one form of a modified erythropoietin mutant protein over another, this noncompatibility can indicate therapeutic differences which in turn can reflect structural, biochemical and biological modifications in the various forms of the modified erythropoietin proteins.
5. An increase in the circulating half-life of EPO in patients which can result in less frequent injections or smaller doses of EPO having to be administered. A prolonged half-life would not only be therapeutically beneficial, but also diminish health care costs in the treatment of chronically ill patients.

Thus, differences in the pharmaceutical characteristics of modified erythropoietin proteins can result in variations in therapeutic effects (e.g., the production of reticulocytes and red blood cells and an increase in hemoglobin synthesis and iron uptake). For example, a difference in the inherent potency which would result in lower bioloads inflicted on the patient's body by administering modified erythropoietin protein which leads to an absence or drastic lowering of side effects (which may endanger the patient's life or make it impossible to administer one form of erythropoietin) is particularly important in high risk patients (e.g., patients with kidney disorders) who are at high risk for hypertension, myocardial infarct or stroke.

Thus, retention, deletion, point mutation or substitution in the 5' and/or 3' UTR sequences of a modified erythropoietin mutein gene fragment can ultimately influence the final structure and chemistry of the protein expressed and secreted by a host cell transfected with that gene fragment. As a consequence the resulting expressed modified erythropoietin mutein protein can exhibit varying biological parameters which can be assessed using bioassays and in therapeutics.

This invention will now be illustrated by the following Examples, which are not intended to be limiting in any way.

EXAMPLE 1

OLIGONUCLEOTIDE-DIRECTED MUTAGENESIS OF HUMAN RECOMBINANT ERYTHROPOIETIN

The oligonucleotide-directed mutagenesis used to prepare the modified secretable human recombinant erythropoietin proteins of the present invention was performed using the Altered Sites™ In Vitro Mutagenesis System (Promega Corporation of Madison, Wis.). The Altered Sites™ system consists of a unique mutagenesis vector and a simple, straightforward procedure for selection of oligonucleotide-directed mutants. The system is based on the use of a second mutagenic oligonucleotide to confer antibiotic resistance to the mutant DNA strand. The system employs a phagemid vector, pSELECT™-1, which contains two genes for antibiotic resistance. One of these genes, for tetracycline resistance, is always functional. The other, for ampicillin resistance, has been inactivated. An oligonucleotide is provided which restores ampicillin resistance to the mutant strand during the mutagenesis reaction. This oligonucleotide is annealed to the single-stranded DNA (ssDNA) template at the same time as the mutagenic oligonucleotide and subsequent synthesis and ligation of the mutant strand links the two. The DNA is transformed into a repair minus strain *E. coli*, or other suitable host, and the cells are grown in the presence of ampicillin, yielding large numbers of colonies. A second round of transformation in JM109, or a similar host, ensures proper segregation of mutant and wild type plasmids and results in a high proportion of mutants.

The pSELECT-1 plasmid is a phagemid, defined as a chimeric plasmid containing the origin of a single-stranded DNA bacteriophage. This phagemid produces ssDNA upon infection of the host cells with the helper phage R408 or M13KO7. The vector contains a multiple cloning site flanked by the SP6 and T7 RNA polymerase promoters and inserted into the lacZ α-peptide. Cloning of a DNA insert into the multiple cloning site results in inactivation of the α-peptide. When plated on indicator plates, colonies containing recombinant plasmids are white in a background of blue colonies. The SP6 and T7 promoters may be used to generate high specific activity RNA probes from either strand of the insert DNA. These sites also serve as convenient priming sites for sequencing of the insert. The pSELECT-1 vector carriers gene sequences for both ampicillin and tetracycline resistance. However, the plasmid is ampicillin sensitive because a frameshift was introduced into this resistance gene by removing the Pst I site. Therefore, propagation of the plasmid and recombinants is performed under tetracycline selection.

The pSELECT-Control vector provides a convenient white/blue positive control for mutagenesis reactions. This vector was derived from the pSELECT-1 vector by removing the Pst I site within the polylinker. The resultant frameshift in the lac α-peptide inactivated β-galactosidase and led to a white colony phenotype on indicator plates. A lacZ repair oligonucleotide (supplied with the system) may be used to introduce a four base insertion which corrects the defect in the lacZ gene and restores colony color to blue. The fraction of blue colonies obtained is an indication of the mutagenesis efficiency. When the lacz repair oligonucleotide is used in combination with the ampicillin repair oligonucleotide to correct this defect, 80–90% of the ampicillin resistant colonies are blue. When the lacZ repair oligonucleotide is used alone, a mutagenesis efficiency of only 2–5% is seen.

The mutagenic oligonucleotide must be complementary to the single-stranded target DNA. The ssDNA produced by the pSELECT-1 phagemid is complementary to the lacZ coding strand.

The stability of the complex between the oligonucleotide and the template is determined by the base composition of the oligonucleotide and the conditions under which it is annealed. In general, a 17–20 base oligonucleotide with the mismatch located in the center will be sufficient for single base mutations. This gives 8–10 perfectly matched nucleotides on either side of the mismatch. For mutations involving two or more mismatches, oligonucleotides of 25 bases or longer are needed to allow for 12–15 perfectly matched nucleotides on either side of the mismatch.

Routinely, oligonucleotides can be annealed by heating to 70° C. for 5 minutes followed by slow cooling to room temperature.

DNA to be mutated is cloned into the pSELECT-1 vector using the multiple cloning sites. The vector DNA is then transformed into competent cells of JM109, or a similar host, and recombinant colonies are selected by plating on LB plates containing 15 μg/ml tetracycline, 0.5 mM IPTG, and 40 μg/ml X-Gal. After incubation for 24 hours at 37° C., colonies containing recombinant plasmids will appear white in a background of blue colonies.

To produce single-stranded template for the mutagenesis reaction, individual colonies containing pSELECT-Control or recombinant pSELECT-1 phagemids are grown and the cultures are infected with helper phage as described below. The single-stranded DNA produced is complementary to the lacZ coding strand and complementary to the strand of the multiple cloning site. Two helper phages R408 and M13KO7 can be used to provide the greatest latitude in optimizing ssDNA yields.

PROTOCOL

1. Prepare an overnight culture of cells containing PSELECT™-1 or PSELECT™-Control phagemid DNA by picking individual tetracycline resistant colonies from a fresh plate. Inoculate 1–2 ml of TYP broth (Promega) containing 15 μg/ml tetracycline and shake at 37° C.
2. The next morning inoculate 5 ml of TYP broth containing 15 μg/ml tetracycline with 100 μl of the overnight culture. Shake vigorously at 37° C. for 30 minutes in a 50 ml tube.
3. Infect the culture with helper phage R408 or M13KO7 at an m.o.i. (multiplicity of infection) of 10 (i.e., add 10 helper phage particles per cell). For the helper phages supplied with this system, add 40 μl. Continue shaking for 6 hours to overnight with vigorous agitation.
4. Harvest the culture supernatant by pelleting the cells at 12,000×g for 15 minutes. Pour the supernatant into a fresh tube and spin again for 15 minutes.
5. Precipitate the phage by adding 0.25 volume of phage precipitation solution (Promega) to the supernatant. Leave on ice for 30 minutes, then centrifuge for 15 minutes at 12,000×g. Thoroughly drain the supernatant.
6. Resuspend the pellet in 400 μl of TE buffer (Promega) and transfer the sample to a microcentrifuge tube.
7. Add 0.4 ml of chloroform:isoamyl alcohol (24:1) to lyse the phage, vortex for 1 full minute, and centrifuge in a microcentrifuge (12,000×g) for 5 minutes. This step removes excess PEG.
8. Transfer the upper, aqueous phase (containing phagemid DNA) to a fresh tube, leaving the interface behind. Add 0.4 ml of TE-saturated phenol:chloroform to the aqueous phase, vortex for 1 full minute, and centrifuge as in step 7.
9. Transfer the upper, aqueous phase to a fresh tube and repeat the phenol extraction as in step 8. If necessary, repeat this extraction several times until there is no visible material at the interface.
10. Transfer the upper, aqueous phase to a fresh tube and add 0.5 volume (200 μl) of 7.5M ammonium acetate plus 2 volumes (1.2 ml) of ethanol. Mix and leave at −20° C. for 30 minutes to precipitate the phagemid DNA.
11. Centrifuge at 12,000×g for 5 minutes, remove the supernatant, carefully rinse the pellet with 70% ethanol, and centrifuge again for 2 minutes. Drain the tube and dry the pellet under vacuum. The pellet may be difficult to see.
12. Resuspend the DNA in 20 μl of $H_2O$. The amount of DNA present can be estimated by agarose gel electrophoresis of a 2 μl sample.

The mutagenesis reaction involves annealing of the ampicillin repair oligonucleotide and the mutagenic oligonucleotide to the ssDNA template, followed by the synthesis of the mutant strand with T4 DNA polymerase. The heteroduplex DNA is then transformed into the repair minus E. coli strain DMH71-18 mutS or other suitable strain. Mutants are selected by overnight growth in the presence of ampicillin. Plasmid DNA is the isolated and transformed into the JM109 strain, or other suitable strain. Mutant, ampicillin resistant colonies may be screened by direct sequencing of the plasmid DNA.

A. ANNEALING REACTION AND MUTANT STRAND SYNTHESIS

The amount of oligonucleotide required in this reaction may vary depending on the size and amount of the single-stranded DNA template. The ampicillin repair oligonucleotide (27 bases long) should be used at a 5:1 oligo:template ratio and the mutagenic oligonucleotide should be used at a 25:1 oligo:template ratio. A typical reaction may contain approximately 100 ng (0.05 pmol) of ssDNA.

PROTOCOL

1. Prepare the mutagenesis or control annealing reactions as described below.

| MUTAGENESIS ANNEALING REACTION | |
|---|---|
| Recombinant pSELECT ™-1 ssDNA | 0.05 pmol |
| Ampicillin repair oligonucleotide (2.2 ng/μl) | 1μ (0.25 pmol) |
| Mutagenic oligonucleotide, phosphorylated (see Table 1) | 1.25 pmol |
| 10X Annealing buffer | 2 μl |
| Sterile $H_2O$ | to final volume 20 μl |

-continued

| CONTROL ANNEALING REACTION | |
|---|---|
| pSELECT ™-Control ssDNA | 100 ng (0.05 pmol) |
| Ampicillin repair oligonucleotide (2.2 ng/µl) | 1 µl (0.25 pmol) |
| lacZ control oligonucleotide (10.8 ng/µl) | 1 µl (1.25 pmol) |
| 10X Annealing buffer | 2 µl |
| Sterile H$_2$O | to final volume 20 µl |

2. Heat the annealing reaction to 70° C. for 5 minutes and allow it to cool slowly to room temperature (15–20 minutes).
3. Place the annealing reaction on ice and add the following:

| 10X Synthesis buffer | 3 µl |
|---|---|
| T4 DNA polymerase (10u/µl) | 1 µl |
| T4 DNA ligase (2u/µl) | 1 µl |
| Sterile H$_2$O | 5 µl |
| | to final volume 20 µl |

4. Incubate the reaction at 37° C. for 90 minutes to perform mutant strand synthesis and ligation.

TABLE 1

AMOUNT OF MUTAGENIC OLIGONUCLEOTIDE NEEDED TO EQUAL 1.25 PMOL

| Primer Length | ng of Primer Equal to 1.25 pmol |
|---|---|
| 17mer | 7.0 ng |
| 20mer | 8.3 ng |
| 23mer | 9.5 ng |
| 26mer | 10.8 ng |
| 29mer | 12.0 ng |

B. TRANSFORMATION INTO BMH 71-18 MUTS

PROTOCOL

1. Add 3 µl of DMSO to 200 µl of BMH71-18 mut S competent cells, mix briefly, and then add the entire synthesis reaction from step A.4.
2. Let the cells sit on ice for 30 minutes.
3. OPTIONAL: For some strains, a heat shock at 42° C. for 1–2 minutes after the incubation on ice has been reported to increase transformation efficiency. In our experience, however, a heat shock does not significantly affect the efficiency of transforming BMH71-18 mut S.
4. Add 4 ml of LB medium and incubate at 37° C. for 1 hour to allow the cells to recover.
5. Add ampicillin to a final concentration of 125 µg/ml and incubate at 37° C. for 12–14 hours with shaking.

NOTE: As a control to check the synthesis reaction, 1 ml of the culture can be removed after the one hour recovery step, spun down, resuspended in 50 µl of LB medium, and plated on LB plates containing 125 µg/ml ampicillin. This is a check for the presence of ampicillin resistant transformants; a second round of transformation is necessary before screening for mutants.

C. PLASMID MINI-PREP PROCEDURE

This procedure is used to isolate pSELECT-1 or pSELECT-Control plasmid DNA from the overnight culture of BMH 71-18 mut S (step B.5, above). A yield of 1–3 µg of plasmid DNA may be expected.

PROTOCOL

1. Place 1.5 ml of the overnight culture into a microcentrifuge tube and centrifuge at 12,000×g for 1 minute. The remainder of the overnight culture can be stored at 4° C.
2. Remove the medium by aspiration, leaving the bacterial pellet as dry as possible.
3. Resuspend the pellet by vortexing in 100 µl of ice-cold miniprep lysis buffer (Promega).
4. Incubate for 5 minutes at room temperature.
5. Add 200 µl of a freshly prepared solution containing 0.2N NaOH, 1% SDS. Mix by inversion. DO NOT VORTEX. Incubate for 5 minutes on ice.
6. Add 150 µl of ice-cold potassium acetate solution, pH 4.8 (Promega). Mix by inversion or gentle vortexing for 10 seconds. Incubate for 5 minutes on ice.
7. Centrifuge at 12,000×g for 5 minutes.
8. Transfer the supernatant to a fresh tube, avoiding the white precipitate.
9. Add 1 volume of TE-saturated phenol/chloroform (Promega). Vortex for 1 minute and centrifuge at 12,000×g for 5 minutes.
10. Transfer the upper, aqueous phase to a fresh tube and add 1 volume of chloroform:isoamyl alcohol)24:1). Vortex for 1 minute and centrifuge as in step 9.
11. Transfer the upper, aqueous phase to a fresh tube and add 2.5 volumes of 100% ethanol. Mix and allow to precipitate 5 minutes on dry ice.
12. Centrifuge at 12,000×g for 5 minutes. Rinse the pellet with 70% ethanol (prechilled) and dry the pellet under vacuum.
13. Dissolve the pellet in 50 µl of sterile deionized water. Add 0.5 µl of 100 µg/ml DNase-free RNase A (Promega) and incubate for 5 minutes at room temperature.
14. The yield of plasmid DNA can be determined by electrophoresis on an agarose gel.

D. TRANSFORMATION INTO JM109 HOST CELLS

PROTOCOL

1. Add 3 µl of DMSO to 200 µl of JM109 competent cells, mix briefly, and add 0.05–0.10 µg of plasmid DNA from step C.14. Other suitable host cells may be used.
2. Let the cells sit on ice for 30 minutes.
3. OPTIONAL: A heat shock may be performed at this step.
4. Add 2 ml of LB medium and incubate at 37° C. for 1 hour to allow the cells to recover.
5. Divide the culture into two microcentrifuge tubes and spin for 1 minute in a microcentrifuge.
6. Pour off the supernatant and resuspended the cells in each tube in 50 µl of LB medium.
7. Plate the cells in each tube on an LB plate containing 125 µg/ml ampicillin and incubate at 37° C. for 12–14 hours.

E. ANALYSIS OF TRANSFORMANTS

The Altered Sites mutagenesis procedure generally produces greater than 50% mutants, so colonies may be screened by direct sequencing. A good strategy is to pick 10 colonies and start by sequencing 4 of these. If the mutation is located within 200–300 bases of either end of the DNA insert, the SP6 or T7 sequencing primers may be used for convenient priming of the sequencing reactions.

EXAMPLE 2

CELL CULTURE AND TRANSFECTION

COS-7 cells were obtained from the American Type Culture Collection (Rockville, Md.) and maintained in Dulbecco's modified Eagle's medium containing 10% fetal bovine serum (GIBCO). Transient expression of cDNAs was performed using a DEAE-Dextran protocol modified by 0.1 mM chloroquine treatment (Sussman, D. J. & Milman, *Mol. Cell Biol.* 4:1641–1645 (1984); Ausubel, F. M., et al., "Current Protocols in Molecular Biology" pp.921–926, John Wiley and Son, New York, (1989)). 3 days before the transfection, COS-7 cells were plated at $2\times10^5$/10-cm tissue culture dish. 4 µg DNA were used in each transfection. Medium was collected 3 days after transfection and assayed for erythropoietin activity and protein.

EXAMPLE 3

IMMUNOPRECIPITATION OF ERYTHROPOIETIN

Wildtype and mutant erythropoietin contained in supernatant medium from COS cell transfections were diluted one- to four-fold with Dulbecco's modified Eagle medium containing 10% fetal bovine serum. After one hour incubation at 37 degrees C with a monoclonal anti-peptide antibody to erythropoietin directed against amino acids 1–26 or 99–129, an equal volume of Omnisorb (Calbiochem) was added to the samples and the suspension was incubated for one hour at 4 degrees C. The Omnisorb was pelleted by centrifugation at 4000 rpm for 30 seconds. The erythropoietin remaining in the supernatant which was not bound by the monoclonal antibody was measured by radioimmunoassay. The amount of erythropoietin bound by antibody (as a percent) was calculated by subtracting the amount in the supernatant from 100%, the starting concentration.

EXAMPLE 4

MODIFIED ERYTHROPOIETIN VARIANT PROTEINS PRODUCED BY ALTERING NONCODING REGIONS OF THE GENE

Typically, variants of recombinant proteins are made by deleting, adding or substituting nucleotides within the coding of the gene. However, it is also possible to make variants of recombinant proteins by altering the noncoding regions of genes, i.e., the 5' and 3' untranslated regions (UTR). Modifications in the UTR of a gene, especially in the 5' sequence as well as in the first intron, influence the regulation of translation; and, thus, the expression of proteins (Schultz, D. E., et al., *J. Virol.* 70:1041–1049, 1996; Kozak, M., *J. Mol. Biol.* 235:95–110, 1994; Bettany, A. J., et al., *J. Biol. Chem.* 267:16531–16537, 1992; Kozak, M., *J. Biol. Chem.* 266:19867–19870, 1991).

Alterations in the non-coding sequences of the erythropoietin gene can result in different mRNA secondary structure (e.g., free energy of the loop and base pairs), translation efficiency; and subsequently, the expression, secretion and biological activity of the erythropoietin. Therefore, different forms of modified erythropoietin proteins can be manufactured as a result of modifications in regions which flank either the 5' or 3' side of the coding region of the erythropoietin gene.

Figure 7:
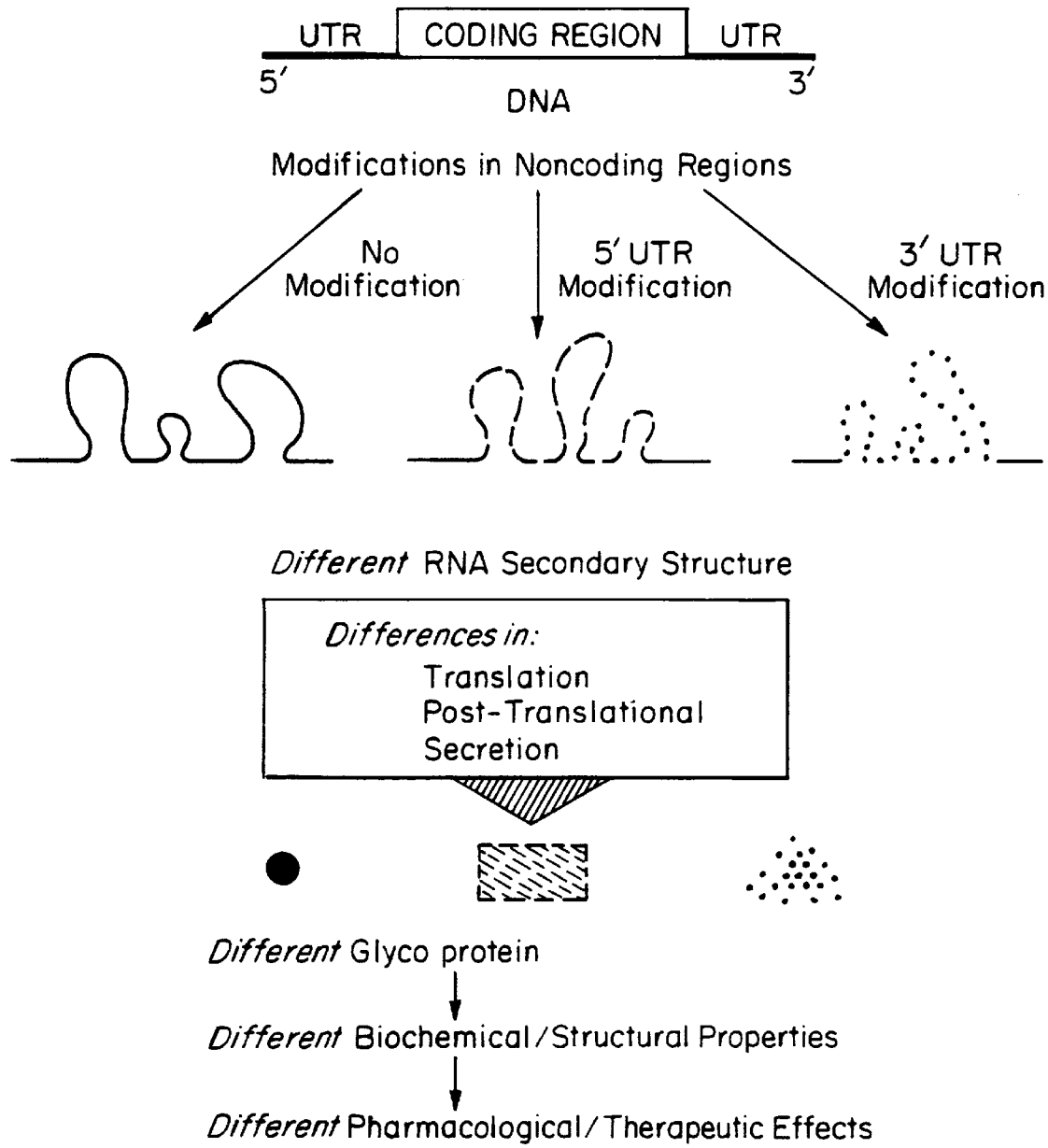
FIG. 7 is a schematic representation discribing how differences in mRNA and protein structure; and protein function can result from alterations in the 5' and 3' UTR of a gene.

FIG. 7 is a schematic representation of changes in mRNA structure and ultimately protein structure and function that can result when an alteration(s) is made in the 5' and/or 3' UTR of the erythropoietin gene. Variations in the modified erythropoietin proteins can be produced as, for example, different restriction enzyme generated fragments of genomic sequences and/or specific nucleotide substitutions and mutations in the 5' and/or 3' UTR of the erythropoietin coding sequence. Oligonucleotide-directed site-specific mutagenesis procedures as described herein can be employed to provide the modified erythropoietin variant proteins.

Alterations in the noncoding regions of the erythropoietin gene can affect mRNA stability, rates of translation, expression from host cells, protein processing, export from rough endoplasmic reticulum, extent and pattern of glycosylation, secretion dynamics and rates of export from the cell. For example, varied glycosylation patterns can result, which, for erythropoietin, are of great importance for biological activity (Yamaguchi, K., et al., *J. Biol. Chem.* 266:20434–20439, 1991). The resulting proteins can represent chemically, structurally and biologically distinct forms of the modified erythropoietin variant proteins.

The nucleotide sequences of the modified erythropoietin variant proteins can be confirmed by DNA sequencing using standard experimental procedures. Distinctive versions of genomic erythropoietin can be produced by mutations in the 5' and 3' UTR and detected by Southern blotting. Likewise, different mRNAs can be identified by Northern blotting. Differences in hybridization conditions, i.e., high or low stringencies, will be an index of the diversity of the DNA and mRNA. It is possible that different genomic sequences may require different promoters (e.g., mouse metallothionein or 3-phosphoglycerate), vectors (e.g., bovine papilloma virus), and/or host cells (e.g., CHO, BHK-21 or C127 cells) to adequately express the modified erythropoietin variant proteins. The technical methods which can be employed for the above mentioned experimental strategies are familiar to those of skill in the art. For example, detailed protocols can be found in Sambrook, et al., "Molecular Cloning: A Laboratory Manual," (1989) and Ausubel, et al., "Current Protocols in Molecular Biology," (1995); Powell, J. S., et al., *Proc. Natl. Acad. Sci. USA* 83:6465–6469, 1986; Sytkowski and Grodberg, (U.S. Pat. No. 5,614,184); Sytkowski (U.S. Pat. No. 5,580,853); and Powell (U.S. Pat. No. 5,688,679); the teachings of which are herein incorporated by reference in their entirety.

Mutations in the 5' and/or 3' UTR of the erythropoietin gene can result in altered RNA structure, total free energy, stability and/or rates and efficiency of translation (Schultz, D. E., et al., *J. Virol.* 70:1041–1049, 1996; Kozak, M., *J. Mol. Biol.* 235:95–110, 1994; Bettany, A. J., et al., *J. Biol. Chem.* 267:16531–16537, 1992; Kozak, M., *J. Biol. Chem.* 266:19867–19870, 1991; Purvis, I. J., et al., *Nucleic Acids Res.* 15: 7951–62, 1987). The secondary structure of mRNAs play an important role in the initiation and efficiency of translation and, thus, in protein synthesis.

Computer modeling using the PC/Gene® RNAFOLD program (IntelliGenetics, Inc.) is used to predict differences in RNA secondary structure, specifically the total free energy, following deletion in the 5' or 3' UTR of, for example, the erythropoietin gene (FIGS. 9–10). The program utilizes an algorithm which calculates the energies of the secondary structure of RNA. It automatically transcribes any DNA sequence into a single stranded RNA sequence. Since the mRNA is single stranded, it can fold back upon itself due to the complementarity of bases resulting in various "loops". Energy must be released to form a basepaired or looped structure and the stability of the resulting secondary structure is determined by the amount of energy released. Therefore, if alternative structures have a free energy of formation of −50 kcal/mol and −100 kcal/mol, the latter structure is intrinsically more likely to be formed.

For example, the free energy for RNA secondary structure for nucleotides 401–624 in the 5' UTR of the erythropoietin gene is predicted to be −161.0 kcal/mol (SEQ ID NO:24). A 50 nucleotide deletion spanning nucleotides 501–550 results in a total free energy of −127.2 kcal/mol (SEQ ID NO:25), whereas a 50 nucleotide deletion at nucleotides 551–600 (SEQ ID NO:26) results in an RNA structure with −118.9 kcal/mol of free energy indicating the importance of the size of the deletion and location in ultimately defining mRNA secondary structure. Larger deletions, in different portions of the 401–624 region of the 5' UTR, yield RNA structures with varying predicted energy states (SEQ ID NOS:27–29). These results are summarized in Table 2.

TABLE 2

SEQUENCE VARIATION IN 5' UTR-
EFFECT ON mRNA FREE ENERGY

| Sequence | SEQ ID NO: | Nucleotide Length (bp) | Region of Deletion | Number of Nucleotides Deleted (bp) | Free Energy (kal/mol) |
|---|---|---|---|---|---|
| Native | 24 | 224 | — | — | −161.0 |
| 5'a | 25 | 174 | 501–550 | 50 | −127.2 |
| 5'b | 26 | 174 | 551–600 | 50 | −118.9 |
| 5'c | 27 | 124 | 401–550 | 100 | −94.1 |
| 5'd | 28 | 74 | 401–550 | 150 | −52.3 |
| 5'e | 29 | 34 | 401–590 | 190 | −11.3 |

Likewise, for example, the free energy of RNA secondary structure for nucleotides 2773–2972 in the 3' UTR of the eryhthropoietin gene is predicted to be −81.4 kcal/mol (SEQ ID NO:30). A 50 nucleotide deletion spanning nucleotides 2923–2972 (SEQ ID NO:31) results in a total free energy of −53.5 kcal/mol, whereas a 100 nucleotide deletion at nucleotides 2873–2972 (SEQ ID NO:32) results in an RNA structure with −33.3 kcal/mol of free energy. Larger deletions, in different portions of the 2773–2973 region of the 3' UTR, yield RNA structures with varying predicted energy states (SEQ ID NOS:33 and 34). These results are summarized in Table 3.

TABLE 3

SEQUENCE VARIATION IN 3' UTR-
EFFECT ON mRNA FREE ENERGY

| Sequence | SEQ ID NO: | Nucleotide Length (bp) | Region of Deletion | Number of Nucleotides Deleted (bp) | Free Energy (kal/mol) |
|---|---|---|---|---|---|
| Native | 30 | 200 | — | — | −81.4 |
| 3'a | 31 | 150 | 2923–2972 | 50 | −53.5 |
| 3'b | 32 | 100 | 2873–2972 | 100 | −33.3 |
| 3'c | 33 | 50 | 2823–2972 | 150 | −12.5 |
| 3'd | 34 | 100 | 2801–2900 | 100 | −36.6 |

The secondary structure of mRNA affects the rates of translation of the corresponding coding regions (Kikinis, Z., et al., *Nucleic Acids Res.* 23: 4190–4195, 1995; Kozak, M., *Mamm. Genome* 7: 563–574, 1996; Bettany, A. J., et al., *J. Biol. Chem.* 267: 16531–16537, 1992; Kozak, M., *J. Mol. Biol.* 235: 95–110, 1994). Secondary structure loops in the mRNA must be unwound to facilitate ribosome attachment and proper protein assembly (Alberts, B., et al., *"Molecular Biology of the Cell"*, 3rd ed., Garland Publishing, Inc., New York, N.Y., pp. 223–290, 1994).

The nascent polypeptide chains can interact with chaperon proteins, for example, BiP, in unique ways which can affect the proper folding of the polypeptide chain and influence passage of the protein through the endoplasmic reticulum thereby altering glycosylation of the resulting protein. Recent data suggest that BiP-like proteins not only bind improperly folded proteins but also may assist in the appropriate protein folding and facilitate the membrane translocation and glycosylation of secretory proteins. (Knittler, M. R., et al., EMBO J.,11:1573–1581, (1992); Sanders, S. L., et al., Cell, 69:353–365, (1992)). Alterations in glycosylation patterns can influence the secretion and, in the case of erythropoietin, drastically alter biological activity (Yamaguchi, K., et al., *J. Biol. Chem.*, 266:20434–20439, 1991).

The three dimensional structure of erythropoietin is significantly influenced by the protein backbone and the oligosaccharide chains. Alterations in the carbohydrate composition (e.g., the number of N- or O-linked oligosaccharide residues and/or type of sugar moieties) can lead to different biological properties of the modified erythropoietin variant proteins and, thus, different therapeutic effects. Therefore, an alteration in the 5' or 3' UTR can affect mRNA secondary structure, which in turn can influence the rate of expression and post-translational modifications such as glycosylation. The proper glycosylation of erythropoietin is of paramount importance to proper folding and secretion of the mature product and, hence, its biological and pharmacological properties.

Indices of intrinsic structural variations in the modified erythropoietin proteins can be manifested in differences in the three-dimensional structure of the protein backbone and the extent and pattern of carbohydrate chains. For example, circular dichroism (CD) spectra and thermal stability for the resulting erythropoietin mutant proteins can be performed to determine the content of alpha helix, beta sheet, beta turn and random coil for different glycoproteins. The structure of the oligosaccharide chains can be determined, for example, using enzymatic and chemical deglycosylation, gas chromatography, methylation analyses, fast-atom-bombardment mass spectrometry as well as one-and two-dimensional $^1$H-NMR spectrometry. The methods to perform the above mentioned analyses are routine to one of ordinary skill in the art and are delineated in detail in several references including for example, Ausubel, F. M., et al., *"Current Protocols in Molecular Biology"* (1995); Nimtz, M., et al. *Eur. J. Biochem.* 213: 39–56, 1993; and Nimtz, M., et al., FEBS 365: 203–208, 1995, the teachings of which are herein incorporated by reference in their entirety.

In addition, assessment of the structural differences in the modified erythropoietin variant proteins can be evaluated using immunoprecipitation with erythropoietin-specific monoclonal antibodies and heat denaturation curves. Experimental techniques to measure these properties of erythropoietin are described in Sytkowski and Grodberg (U.S. Pat. No. 5,614,184); Sytkowski (U.S. Pat. No. 5,580,853); and Powell (U.S. Pat. No. 5,688,679); the teachings of which are herein incorporated by reference in their entirety.

EXAMPLE 5

EVALUATION OF BIOLOGICAL ACTIVITY OF MODIFIED ERYTHROPOIETIN VARIANT PROTEINS

The biological activity of the modified erythropoietin variant proteins is determined using in vitro and in vivo assays.

The modified erythropoietin variant proteins can be preferably purified substantially prior to use, particularly where the protein could be employed as an in vivo therapeutic, although the degree of purity is not necessarily critical where the molecule is to be used in vitro. The modified erythropoietin variant proteins can be isolated to about 50% purity (by weight), more preferably to about 80% by weight or about 95% by weight. It is most preferred to utilize a protein which is essentially pure (e.g., about 99% by weight or to homogeneity) for in vitro and in vivo assays as well as in vivo therapeutics.

For example, the modified erythropoietin variant proteins, which are prepared according to the methods discussed in the Examples, can be screened for in vitro and in vivo activity prior to use in therapeutic settings. The in vitro assay measures the effect of erythropoietin variant proteins on erythropoiesis in intact mouse spleen cells according to the procedure of Krystal, G., *Exp. Hematol.* 11:649–660 (1983). To screen the various modified erythropoietin variant proteins for activity, for example, in vitro or in vivo, the proteins (or mixtures of the modified erythropoietin variant proteins) can be evaluated for the extent of erythropoiesis or receptor binding. Tests to determine biological activity are well-known to those of skill in the art. For example, the biological activity of erythropoietin can be measured as described in Sytkowski and Grodberg (U.S. Pat. No. 5,614,184); Sytkowski (U.S. Pat. No. 5,580,853); Sytkowski, U.S. patent application "Modified Polypeptides with Altered Biological Activity", filed Feb. 3, 1998; and Powell (U.S. Pat. No. 5,688,679); the teachings of which are herein incorporated by reference in their entirety.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

SEQUENCE LISTING

```
<160> NUMBER OF SEQ ID NOS: 34

<210> SEQ ID NO 1
<211> LENGTH: 10
<212> TYPE: PRT
<213> ORGANISM: Artificial Sequence
<220> FEATURE:
<223> OTHER INFORMATION: Artificial correspondence to human amino acid
      sequence.

<400> SEQUENCE: 1

Ser Gly Leu Arg Ser Leu Thr Thr Leu Leu
1               5                   10

<210> SEQ ID NO 2
<211> LENGTH: 18
<212> TYPE: PRT
<213> ORGANISM: Artificial Sequence
<220> FEATURE:
<223> OTHER INFORMATION: Artificial correspondence to human amino acid
      sequence.

<400> SEQUENCE: 2

Asp Lys Thr Val Ser Gly Leu Arg Ser Leu Thr Thr Leu Leu Arg Ala
1               5                   10                  15

Leu Gly

<210> SEQ ID NO 3
<211> LENGTH: 58
<212> TYPE: DNA
<213> ORGANISM: Artificial Sequence
<220> FEATURE:
<223> OTHER INFORMATION: Synthetic oligonucleotide encoding protein
      mutant.

<400> SEQUENCE: 3
ggataaagcc gtcagtggcc ttcgcagcct caccactctg cttcgggctc tgggagcc        58

<210> SEQ ID NO 4
<211> LENGTH: 47
```

```
<212> TYPE: DNA
<213> ORGANISM: Artificial Sequence
<220> FEATURE:
<223> OTHER INFORMATION: Synthetic oligonucleotide encoding protein
      mutant.

<400> SEQUENCE: 4
ggataaagcc gtcgctggcc ttcgcagcct cacgactctg cttcggg          47

<210> SEQ ID NO 5
<211> LENGTH: 40
<212> TYPE: DNA
<213> ORGANISM: Artificial Sequence
<220> FEATURE:
<223> OTHER INFORMATION: Synthetic oligonucleotide encoding protein
      mutant.

<400> SEQUENCE: 5
gccgtcagtg cccttcgcag cctcacgact ctgcttcggg                   40

<210> SEQ ID NO 6
<211> LENGTH: 27
<212> TYPE: DNA
<213> ORGANISM: Artificial Sequence
<220> FEATURE:
<223> OTHER INFORMATION: Synthetic oligonucleotide encoding protein
      mutant.

<400> SEQUENCE: 6
gccgtcagtg gcgctcgcag cctcacc                                 27

<210> SEQ ID NO 7
<211> LENGTH: 37
<212> TYPE: DNA
<213> ORGANISM: Artificial Sequence
<220> FEATURE:
<223> OTHER INFORMATION: Synthetic oligonucleotide encoding protein
      mutant.

<400> SEQUENCE: 7
cgtcagtggc cttgccagcc tcacgactct gcttcgg                      37

<210> SEQ ID NO 8
<211> LENGTH: 37
<212> TYPE: DNA
<213> ORGANISM: Artificial Sequence
<220> FEATURE:
<223> OTHER INFORMATION: Synthetic oligonucleotide encoding protein
      mutant.

<400> SEQUENCE: 8
cgtcagtggc cttgacagcc tcacgactct gcttcgg                      37

<210> SEQ ID NO 9
<211> LENGTH: 31
<212> TYPE: DNA
<213> ORGANISM: Artificial Sequence
<220> FEATURE:
<223> OTHER INFORMATION: Synthetic oligonucleotide encoding protein
      mutant.

<400> SEQUENCE: 9
ggccttcgca gcgccacgac tctgcttcgg g                            31

<210> SEQ ID NO 10
<211> LENGTH: 31
<212> TYPE: DNA
```

```
<213> ORGANISM: Artificial Sequence
<220> FEATURE:
<223> OTHER INFORMATION: Synthetic oligonucleotide encoding protein
      mutant.

<400> SEQUENCE: 10
gccttcgcag cctcgcgact ctgcttcggg c                          31

<210> SEQ ID NO 11
<211> LENGTH: 36
<212> TYPE: DNA
<213> ORGANISM: Artificial Sequence
<220> FEATURE:
<223> OTHER INFORMATION: Synthetic oligonucleotide encoding protein
      mutant.

<400> SEQUENCE: 11
cgcagcctca ccgctctgct tcgagctctg cgagcc                     36

<210> SEQ ID NO 12
<211> LENGTH: 31
<212> TYPE: DNA
<213> ORGANISM: Artificial Sequence
<220> FEATURE:
<223> OTHER INFORMATION: Synthetic oligonucleotide encoding protein
      mutant.

<400> SEQUENCE: 12
gcctcaccac tgccttcgag ctctgcgagc c                          31

<210> SEQ ID NO 13
<211> LENGTH: 27
<212> TYPE: DNA
<213> ORGANISM: Artificial Sequence
<220> FEATURE:
<223> OTHER INFORMATION: Synthetic oligonucleotide encoding protein
      mutant.

<400> SEQUENCE: 13
cctcaccact ctggctcggg ctctgcg                               27

<210> SEQ ID NO 14
<211> LENGTH: 30
<212> TYPE: DNA
<213> ORGANISM: Artificial Sequence
<220> FEATURE:
<223> OTHER INFORMATION: Synthetic oligonucleotide encoding protein
      mutant.

<400> SEQUENCE: 14
gtggccttcg cgccctcacg actctgcttc                            30

<210> SEQ ID NO 15
<211> LENGTH: 30
<212> TYPE: DNA
<213> ORGANISM: Artificial Sequence
<220> FEATURE:
<223> OTHER INFORMATION: Synthetic oligonucleotide encoding protein
      mutant.

<400> SEQUENCE: 15
cctcaccact gcgcttcgag ctctgggagc                            30

<210> SEQ ID NO 16
<211> LENGTH: 27
<212> TYPE: DNA
<213> ORGANISM: Artificial Sequence
```

```
<220> FEATURE:
<223> OTHER INFORMATION: Synthetic oligonucleotide encoding protein
      mutant.

<400> SEQUENCE: 16
cctcaccact ctggctcggg ctctggg                                              27

<210> SEQ ID NO 17
<211> LENGTH: 37
<212> TYPE: DNA
<213> ORGANISM: Artificial Sequence
<220> FEATURE:
<223> OTHER INFORMATION: Synthetic oligonucleotide encoding protein
      mutant.

<400> SEQUENCE: 17
cgtcagtggc cttaacagcc tcacgactct gcttcgg                                   37

<210> SEQ ID NO 18
<211> LENGTH: 37
<212> TYPE: DNA
<213> ORGANISM: Artificial Sequence
<220> FEATURE:
<223> OTHER INFORMATION: Synthetic oligonucleotide encoding protein
      mutant.

<400> SEQUENCE: 18
cgtcagtggc cttgagagcc tcacgactct gcttcgg                                   37

<210> SEQ ID NO 19
<211> LENGTH: 37
<212> TYPE: DNA
<213> ORGANISM: Artificial Sequence
<220> FEATURE:
<223> OTHER INFORMATION: Synthetic oligonucleotide encoding protein
      mutant.

<400> SEQUENCE: 19
cgtcagtggc cttcagagcc tcacgactct gcttcgg                                   37

<210> SEQ ID NO 20
<211> LENGTH: 37
<212> TYPE: DNA
<213> ORGANISM: Artificial Sequence
<220> FEATURE:
<223> OTHER INFORMATION: Synthetic oligonucleotide encoding protein
      mutant.

<400> SEQUENCE: 20
cgtcagtggc cttcacagcc tcacgactct gcttcgg                                   37

<210> SEQ ID NO 21
<211> LENGTH: 37
<212> TYPE: DNA
<213> ORGANISM: Artificial Sequence
<220> FEATURE:
<223> OTHER INFORMATION: Synthetic oligonucleotide encoding protein
      mutant.

<400> SEQUENCE: 21
cgtcagtggc cttctcagcc tcacgactct gcttcgg                                   37

<210> SEQ ID NO 22
<211> LENGTH: 37
<212> TYPE: DNA
<213> ORGANISM: Artificial Sequence
<220> FEATURE:
```

<223> OTHER INFORMATION: Synthetic oligonucleotide encoding protein mutant.

<400> SEQUENCE: 22
cgtcagtggc ctgaagagcc tcacgactct gcttcgg           37

<210> SEQ ID NO 23
<211> LENGTH: 3601
<212> TYPE: DNA
<213> ORGANISM: Homo sapien

<400> SEQUENCE: 23

| | | | | | |
|---|---|---|---|---|---|
| aagcttctgg | gcttccagac | ccagctactt | tgcggaactc | agcaacccag | gcatctctga | 60 |
| gtctccgccc | aagaccggga | tgcccccccag | gggaggtgtc | cggagcccca | gcctttccca | 120 |
| gatagcacgc | tccgccagtc | ccaagggtgc | gcaaccggct | gcactcccct | cccgcgaccc | 180 |
| agggcccggg | agcagccccc | atgacccaca | cgcacgtctg | cagcagcccc | gctcacgccc | 240 |
| cggcgagcct | caacccaggc | gtcctgcccc | tgctctgacc | ccgggtggcc | cctacccctg | 300 |
| gcgacccctc | acgcacacag | cctctcccccc | accccaccc | gcgcacgcac | acatgcagat | 360 |
| aacagccccg | accccggcc | agagccgcag | agtccctggg | ccaccccggc | cgctcgctgc | 420 |
| gctgcgccgc | accgcgctgt | cctcccgagc | ccggaccggg | gccaccgcgc | ccgctctgct | 480 |
| ccgacaccgc | gccccctgga | cagccgccct | ctcctctagg | cccgtggggc | tggccctgca | 540 |
| ccgccgagct | tcccgggatg | agggcccccg | gtgtggtcac | ccggcgcgcc | ccaggtcgct | 600 |
| gagggacccc | ggccaggcgc | ggagatgggg | tgcacggtga | gtactcgcgg | gctgggcgct | 660 |
| cccgccgccc | gggtccctgt | ttgagcgggg | atttagcgcc | ccggctattg | gccaggaggt | 720 |
| ggctgggttc | aaggaccggc | gacttgtcaa | ggaccccgga | agggggaggg | gggtggggca | 780 |
| gcctccacgt | gccagcgggg | acttgggga | gtccttgggg | atggcaaaaa | cctgacctgt | 840 |
| gaaggggaca | cagtttgggg | gttgagggga | agaaggtttg | ggggttctgc | tgtgccagtg | 900 |
| gagaggaagc | tgataagctg | ataacctggg | cgctggagcc | accacttatc | tgccagaggg | 960 |
| gaagcctctg | tcacaccagg | attgaagttt | ggccggagaa | gtggatgctg | gtagctgggg | 1020 |
| gtggggtgtg | cacacggcag | caggattgaa | tgaaggccag | ggaggcagca | cctgagtgct | 1080 |
| tgcatggttg | gggacaggaa | ggacgagctg | gggcagagac | gtggggatga | aggaagctgt | 1140 |
| ccttccacag | ccaccttct | ccctccccgc | ctgactctca | gcctggctat | ctgttctaga | 1200 |
| atgtcctgcc | tggctgtggc | ttctcctgtc | cctgctgtcg | ctccctctgg | gcctcccagt | 1260 |
| cctgggcgcc | ccaccacgcc | tcatctgtga | cagccgagtc | ctggagaggt | acctcttgga | 1320 |
| ggccaaggag | gccgagaata | tcacggtgag | acccctttccc | cagcacattc | cacagaactc | 1380 |
| acgctcaggg | cttcagggaa | ctcctcccag | atccaggaac | ctggcacttg | gtttggggtg | 1440 |
| gagttgggaa | gctagacact | gccccctac | ataagaataa | gtctggtggc | cccaaaccat | 1500 |
| acctggaaac | taggcaagga | gcaaagccag | cagatcctac | ggcctgtggg | ccagggccag | 1560 |
| agccttcagg | gacccttgac | tccccgggct | gtgtgcattt | cagacgggct | gtgctgaaca | 1620 |
| ctgcagcttg | aatgagaata | tcactgtccc | agacaccaaa | gttaatttct | atgcctggaa | 1680 |
| gaggatggag | gtgagttcct | ttttttttt | ttttcctttc | ttttggagaa | tctcatttgc | 1740 |
| gagcctgatt | ttggatgaaa | gggagaatga | tcggggaaa | ggtaaatgg | agcagcagag | 1800 |
| atgaggctgc | ctgggcgcag | aggctcacgt | ctataatccc | aggctgagat | ggccgagatg | 1860 |
| ggagaattgc | ttgagccctg | gagtttcaga | ccaacctagg | cagcatagtg | agatccccca | 1920 |

-continued

```
tctctacaaa catttaaaaa aattagtcag gtgaagtggt gcatggtggt agtcccagat     1980
atttggaagg ctgaggcggg aggatcgctt gagcccagga atttgaggct gcagtgagct     2040
gtgatcacac cactgcactc cagcctcagt gacagagtga ggccctgtct caaaaaagaa     2100
aagaaaaaag aaaaataatg agggctgtat ggaatacatt cattattcat tcactcactc     2160
actcactcat tcattcattc attcattcaa caagtcttat tgcatacctt ctgtttgctc     2220
agcttggtgc ttggggctgc tgaggggcag gagggagagg gtgacatggg tcagctgact     2280
cccagagtcc actccctgta ggtcgggcag caggccgtag aagtctggca gggcctggcc     2340
ctgctgtcgg aagctgtcct gcggggccag gccctgttgg tcaactcttc ccagccgtgg     2400
gagcccctgc agctgcatgt ggataaagcc gtcagtggcc ttcgcagcct caccactctg     2460
cttcgggctc tgggagccca ggtgagtagg agcggacact tctgcttgcc ctttctgtaa     2520
gaaggggaga agggtcttgc taaggagtac aggaactgtc cgtattcctt cccttctgt     2580 ggcactgcag cgacctcctg ttttctcctt ggcagaagga agccatctcc cctccagatg     2640
cggcctcagc tgctccactc cgaacaatca ctgctgacac tttccgcaaa ctcttccgag     2700
tctactccaa tttcctccgg ggaaagctga agctgtacac aggggaggcc tgcaggacag     2760
gggacagatg accaggtgtg tccacctggg catatccacc acctccctca ccaacattgc     2820
ttgtgccaca ccctcccccg ccactcctga acccgtcga ggggctctca gctcagcgcc     2880
agcctgtccc atggacactc cagtgccagc aatgacatct caggggccag aggaactgtc     2940
cagagagcaa ctctgagatc taaggatgtc acagggccaa cttgagggcc cagagcagga     3000
agcattcaga gagcagcttt aaactcaggg acagagccat gctgggaaga cgcctgagct     3060
cactcggcac cctgcaaaat tgatgccag gacacgcttt ggaggcgatt tacctgtttt     3120
cgcacctacc atcagggaca ggatgacctg gagaacttag gtggcaagct gtgacttctc     3180
caggtctcac gggcatgggc actcccttgg tggcaagagc ccccttgaca ccgggtggt     3240 gggaaccatg aagacaggat gggggctggc ctctggctct catgggggtcc aagttttgtg     3300 tattcttcaa cctcattgac aagaactgaa accaccaata tgactcttgg cttttctgtt     3360
ttctgggaac ctccaaatcc cctggctctg tcccactcct ggcagcagtg cagcaggtcc     3420
aggtccggga aatgagggggt ggagggggct gggccctacg tgctgtctca cacagcctgt     3480
ctgacctctc gacctaccgg cctaggccac aagctctgcc tacgctggtc aataaggtgt     3540
ctccattcaa ggcctcaccg cagtaaggca gctgccaacc ctgcccaggg caaggctgca    3600
g                                                                      3601
```

```
<210> SEQ ID NO 24
<211> LENGTH: 224
<212> TYPE: DNA
<213> ORGANISM: Artificial Sequence
<220> FEATURE:
<223> OTHER INFORMATION: Portion of 5' untranslated region of human
      erythropoietin

<400> SEQUENCE: 24
```

```
ccaccccggc cgctcgctgc gctgcgccgc accgcgctgt cctcccggag ccggaccggg      60
gccaccgcgc ccgtctgct ccgacaccgc gccccctgga cagccgccct ctcctctagg     120
cccgtggggc tggccctgca ccgccgagct tcccgggatg agggccccg gtgtggtcac     180 ccggcgcgcc ccagtcgct gagggacccc ggccaggcgc ggag                       224
```

```
<210> SEQ ID NO 25
```

<211> LENGTH: 174
<212> TYPE: DNA
<213> ORGANISM: Artificial Sequence
<220> FEATURE:
<223> OTHER INFORMATION: Mutant of a portion of 5' untranslated region
      of human erythropoietin

<400> SEQUENCE: 25
ccaccccggc cgctcgctgc gctgcgccgc accgcgctgt cctcccggag ccggaccggg      60
gccaccgcgc ccgctctgct ccgacaccgc gccccctgga tcccgggatg agggcccccg     120
gtgtggtcac ccggcgcgcc ccaggtcgct gagggacccc ggccaggcgc ggag           174

<210> SEQ ID NO 26
<211> LENGTH: 174
<212> TYPE: DNA
<213> ORGANISM: Artificial Sequence
<220> FEATURE:
<223> OTHER INFORMATION: Mutant of a portion of 5' untranslated region
      of human erythropoietin

<400> SEQUENCE: 26
ccaccccggc cgctcgctgc gctgcgccgc accgcgctgt cctcccggag ccggaccggg      60
gccaccgcgc ccgctctgct ccgacaccgc gccccctgga cagccgccct ctcctctagg     120
cccgtggggc tggccctgca ccgccagct gagggacccc ggccaggcgc ggag            174

<210> SEQ ID NO 27
<211> LENGTH: 124
<212> TYPE: DNA
<213> ORGANISM: Artificial Sequence
<220> FEATURE:
<223> OTHER INFORMATION: Mutant of a portion of 5' untranslated region
      of human erythropoietin

<400> SEQUENCE: 27
cagccgccct ctcctctagg cccgtggggc tggccctgca ccgccagct tcccgggatg       60 agggcccccg gtgtggtcac ccggcgcgcc ccaggtcgct gagggacccc ggccaggcgc    120
ggag                                                                  124

<210> SEQ ID NO 28
<211> LENGTH: 74
<212> TYPE: DNA
<213> ORGANISM: Artificial Sequence
<220> FEATURE:
<223> OTHER INFORMATION: Mutant of a portion of 5' untranslated region
      of human erythropoietin

<400> SEQUENCE: 28
tcccgggatg agggcccccg gtgtggtcac ccggcgcgcc ccaggtcgct gagggacccc      60
ggccaggcgc ggag                                                        74

<210> SEQ ID NO 29
<211> LENGTH: 34
<212> TYPE: DNA
<213> ORGANISM: Artificial Sequence
<220> FEATURE:
<223> OTHER INFORMATION: Mutant of a portion of 5' untranslated region
      of human erythropoietin

<400> SEQUENCE: 29
ccaggtcgct gagggacccc ggccaggcgc ggag                                  34

<210> SEQ ID NO 30

<210> SEQ ID NO 30
<211> LENGTH: 200
<212> TYPE: DNA
<213> ORGANISM: Artificial Sequence
<220> FEATURE:
<223> OTHER INFORMATION: Portion of 3' untranslated region of human
      erythropoietin

<400> SEQUENCE: 30
ccaggtgtgt ccacctgggc atatccacca cctccctcac caacattgct tgtgccacac      60
cctcccccgc cactcctgaa ccccgtcgag gggctctcag ctcagcgcca gcctgtccca     120
tggacactcc agtgccagca atgacatctc aggggccaga ggaactgtcc agagagcaac     180
tctgagatct aaggatgtca                                                 200

<210> SEQ ID NO 31
<211> LENGTH: 150
<212> TYPE: DNA
<213> ORGANISM: Artificial Sequence
<220> FEATURE:
<223> OTHER INFORMATION: Mutant of a portion of 3' untranslated region
      of human erythropoietin

<400> SEQUENCE: 31
ccaggtgtgt ccacctgggc atatccacca cctccctcac caacattgct tgtgccacac      60
cctcccccgc cactcctgaa ccccgtcgag gggctctcag ctcagcgcca gcctgtccca     120
tggacactcc agtgccagca atgacatctc                                     150

<210> SEQ ID NO 32
<211> LENGTH: 100
<212> TYPE: DNA
<213> ORGANISM: Artificial Sequence
<220> FEATURE:
<223> OTHER INFORMATION: Mutant of a portion of 3' untranslated region
      of human erythropoietin

<400> SEQUENCE: 32
ccaggtgtgt ccacctgggc atatccacca cctccctcac caacattgct tgtgccacac      60
cctcccccgc cactcctgaa ccccgtcgag gggctctcag                           100

<210> SEQ ID NO 33
<211> LENGTH: 50
<212> TYPE: DNA
<213> ORGANISM: Artificial Sequence
<220> FEATURE:
<223> OTHER INFORMATION: Mutant of a portion of 3' untranslated region
      of human erythropoietin

<400> SEQUENCE: 33
ccaggtgtgt ccacctgggc atatccacca cctccctcac caacattgct                 50

<210> SEQ ID NO 34
<211> LENGTH: 100
<212> TYPE: DNA
<213> ORGANISM: Artificial Sequence
<220> FEATURE:
<223> OTHER INFORMATION: Mutant of a portion of 3' untranslated region
      of human erythropoietin

<400> SEQUENCE: 34
ccaggtgtgt ccacctgggc atatccaccc agtgccagca atgacatctc aggggccaga      60
ggaactgtcc agagagcaac tctgagatct aaggatgtca                           100

What is claimed is:

1. A nucleic acid molecule comprising a coding sequence which encodes an erythropoietin protein and at least one sequence selected from the group consisting of a 5' noncoding sequence comprising SEQ ID NOS: 25 or 26 and a 3' noncoding sequence comprising SEQ ID NO: 34.

2. The nucleic acid molecule of claim 1, further comprising one or more mutations in the coding region encoding an erythropoietin protein having an amino acid residue which differs from an amino acid residue in a corresponding position in the wildtype erythropoietin protein selected from the group consisting of amino acid residue 101, amino acid residue 103, amino acid residue 104, amino acid residue 105 and amino acid residue 108.

3. The nucleic acid molecule of claim 2, wherein the mutation in the coding region is a mutation which encodes an alanine at the amino acid residue at position 101.

4. The nucleic acid molecule of claim 2, wherein the mutation in the coding region is a mutation which encodes an amino acid residue at position 103 selected from the group consisting of aspartate alanine, glutamate, histidine and lysine.

5. The nucleic acid molecule of claim 2, wherein the mutation in the coding region is a mutation which encodes an alanine at the amino acid residue at position 104.

6. The nucleic acid molecule of claim 2, wherein the mutation in the coding region is a mutation which encodes an alanine at the amino acid residue at position 105.

7. The nucleic acid molecule of claim 2, wherein the mutation in the coding region is a mutation which encodes an alanine at the amino acid residue at position 108.

8. A recombinant host cell comprising a nucleic acid molecule comprising a coding sequence which encodes an erythropoietin protein and at least one sequence selected from the group consisting of a 5' noncoding sequence comprising SEQ ID NOS: 25 or 26 and a 3' noncoding sequence comprising SEQ ID NO: 34.

9. A method for making an erthropoietin protein, comprising the steps of:

a) transfecting a recombinant host cell with a vector comprising a nucleic acid molecule comprising a coding sequence which encodes an erythropoietin protein and at least one sequence selected from the group consisting of a 5' noncoding sequence comprising SEQ ID NOS: 25 or 26 and a 3' noncoding sequence comprising SEQ ID NO: 34; and b) culturing the recombinant host cell in a suitable medium to produce the erythropoietin protein.

10. The method of claim 9, further comprising recovering the erythropoietin protein from the suitable medium.

11. The method of claim 10, further comprising combining the recovered erythropoietin protein with a pharmaceutically acceptable carrier to produce a pharmaceutical composition.

12. A method for treating a subject, comprising producing a pharmaceutical composition according to the method of claim 11 and administering the composition to the subject.

* * * * *